US010226493B2

(12) United States Patent
Lau et al.

(10) Patent No.: US 10,226,493 B2
(45) Date of Patent: *Mar. 12, 2019

(54) CORIOLUS VERSICOLOR EXTRACTS, METHODS OF PREPARATION AND USES THEREOF

(75) Inventors: Allan Sik Yin Lau, Hong Kong (CN); Stanley Chi Chung Chik, Hong Kong (CN); Anna Hing-Yee Law, Hong Kong (CN); Cindy Lai Hung Yang, Hong Kong (CN); Maureen Lau, legal representative, Hong Kong (CN)

(73) Assignees: BAGI RESEARCH LIMITED, Hong Kong (CN); VERSITECH LIMITED, Hong Kong (CN)

( * ) Notice: Subject to any disclaimer, the term of this patent is extended or adjusted under 35 U.S.C. 154(b) by 89 days.

This patent is subject to a terminal disclaimer.

(21) Appl. No.: 13/876,070

(22) PCT Filed: Oct. 6, 2011
(Under 37 CFR 1.47)

(86) PCT No.: PCT/IB2011/002845
§ 371 (c)(1),
(2), (4) Date: Aug. 23, 2013

(87) PCT Pub. No.: WO2012/046145
PCT Pub. Date: Apr. 12, 2012

(65) Prior Publication Data
US 2014/0017275 A1    Jan. 16, 2014

Related U.S. Application Data

(60) Provisional application No. 61/390,279, filed on Oct. 6, 2010, provisional application No. 61/432,853, filed on Jan. 14, 2011.

(51) Int. Cl.
*A61K 36/07* (2006.01)

(52) U.S. Cl.
CPC ........ *A61K 36/07* (2013.01); *A61K 2236/333* (2013.01); *Y02A 50/463* (2018.01)

(58) Field of Classification Search
None
See application file for complete search history.

(56) References Cited

U.S. PATENT DOCUMENTS

| | | | |
|---|---|---|---|
| 4,229,570 A | 10/1980 | Ueno et al. | |
| 4,699,787 A | 10/1987 | Ueno et al. | |
| 4,851,395 A | 7/1989 | Ueno et al. | |
| 5,824,648 A | 10/1998 | Yang et al. | |
| 6,087,335 A | 7/2000 | Yang et al. | |
| 6,544,564 B1 * | 4/2003 | Farley | A61K 36/07 424/195.15 |
| 2003/0224014 A1 | 12/2003 | Chow et al. | |
| 2004/0029955 A1 * | 2/2004 | Kouge et al. | 514/459 |
| 2006/0073162 A1 | 4/2006 | Chow et al. | |
| 2007/0104727 A1 | 5/2007 | Chan et al. | |
| 2009/0053221 A1 * | 2/2009 | Cheung et al. | 424/133.1 |
| 2010/0092584 A1 * | 4/2010 | Lee | A23L 1/3002 424/740 |

FOREIGN PATENT DOCUMENTS

| | | |
|---|---|---|
| CN | 1459459 A | 12/2003 |
| CN | 101365338 A | 2/2009 |
| EP | 0295962 A2 | 12/1988 |
| JP | 53-6413 | 1/1978 |
| JP | H08-25896 B2 | 3/1996 |
| JP | 2009-514960 | 4/2009 |
| KR | 20080057368 A | 6/2008 |
| WO | WO 2007/056271 A2 | 5/2007 |

OTHER PUBLICATIONS 2008 http://web.archive.org/web/20080616123525/http://my.clevelandclinic.org/heart/disorders/valve/sbe.aspx.*
Monma et al., In vitro inactivation of herpes simplex virus by a biological response modifier, PSK, 1997, Antiviral Research, 35: 131-138.*
Zhou et al., Cytotoxic activities of *Coriolus versicolor* (Yunzhi) extracts on human liver cancer and breast cancer cell line, 2007, African J Biotechnology, 6: 1740-1743.*
Cheng, S. et al., "HIV-1 transactivator protein induction of suppressor of cytokine signaling-2 contributes to dysregulation of IFNγ signaling," 2009, *Blood*, vol. 113, p. 5192-5201.
Collins, R. et al., "Polysaccharopeptide from *Coriolus versicolor* has potential for use against human immunodeficiency virus type 1 infection," 1999, *Advanced Research in PSP*, p. 181-186, Hong Kong Association for Health Care, Hong Kong.
Dong, Y. et al., "In vitro inhibition of proliferation of HL-60 cells by tetrandrine and Coriolus versicolor peptide derived from Chinese medicinal herbs," 1997, *Life Sciences*, vol. 60, p. P1135-P1140.
Kobayashi, H. et al., "Antimetastatic Effects of Psk (Krestin), a Protein-Bound Polysaccharide Obtained from Basidiomycetes—an Overview," 1995, *Cancer Epidemiology Biomarkers and Prevention*, vol. 4, p. 275-281.
Lau, C. et al., "Cytotoxic activities of *Coriolus versicolor* (Yunzhi) extract on human leukemia and lymphoma cells by induction of apoptosis," 2004, *Life Sciences*, vol. 75, p. 797-808.
Law, A. et al., "Role for Nonstructural Protein 1 of Severe Acute Respiratory Syndrome Coronavirus in Chemokine Dysregulation," 2007, *Journal of Virology*, vol. 81, p. 416-422.

(Continued)

*Primary Examiner* — Terry A McKelvey
*Assistant Examiner* — Catheryne Chen
(74) *Attorney, Agent, or Firm* — Saliwanchik, Lloyd & Eisenschenk

(57) ABSTRACT

The subject invention provides *Coriolus versicolor* extracts, pharmaceutical compositions comprising the *Coriolus versicolor* extracts, methods of preparation, and therapeutic uses thereof. Advantageously, the subject *Coriolus versicolor* extract has immunomodulatory, anti-tumor, anti-microbial, and antiviral effects. In a preferred embodiment, the subject invention can be used to inhibit the metastatic spread of cancer cells. In certain preferred embodiments, the subject invention can be used to treat glioblastoma multiforme, nasopharyngeal carcinoma, breast carcinoma, lung carcinoma, prostate cancer, and colon carcinoma, as well as bacterial, viral, fungal, protozoan, and/or other microbial infection.

6 Claims, 13 Drawing Sheets

(56) References Cited

OTHER PUBLICATIONS

Lee, D. et al., "Bioactivity-guided identification and cell signaling technology to delineate the immunomodulatory effects of Panax ginseng on human promonocytic U937 cells," 2009, *Journal of Translational Medicine*, vol. 7, No. 34, p. 1-10.

Liu, R. et al., "Analysis of immunomodulating cytokines mRNAs in the mouse induced by mushroom polysaccharides," 1999, *Life Sciences*, vol. 64, No. 12, p. 1005-1011.

Ng, T. "A review of research on the protein-bound polysaccharide (Polysaccharopeptide, PSP) from the mushroom *Coriolus versicolor* (Basidiomycetes: Polyporaceae," 1998, *General Pharmacology*, vol. 30, No. 1, p. 1-4.

Sakagami, H. et al., "Induction of immunopotentiation activity by a protein-bound polysaccharide, PSK," 1991, *Anticancer Research*, vol. 11, p. 993-999.

Tsukagoshi, S. et al., "Krestin (PSK)." 1984, *Cancer Treatment Reviews*, vol. 11, p. 131-155.

Wang, HX. et al., "Polysaccharide-peptide complexes from the cultured mycelia of the mushroom *Coriolus versicolor* and their culture medium activate mouse lymphocytes and macrophages," 1996, *International Journal of Biochemistry and Cell Biology*, vol. 28, No. 5, p. 601-607.

Yang, Q. et al., "A new biological response modifier substance-PSP," 1993, *Fudan University Press*, p. 247-259, Shanghai, China.

Yang, Q. et al., "Antitumor and Immunomodulating Activities of the Polysaccharide-Peptide (Psp) of Coriolus-Versicolor," 1992, *Eos-Rivista Di Immunologia Ed Immunofarmacologia*, vol. 12, p. 29-34.

Yang, M. et al., "The antitumor effect of a small polypeptide from *Coriolus versicolor*(SPCV)," 1992, *American Journal of Chinese Medicine*, vol. 20, p. 221-232.

\* cited by examiner

CORIOLUS VERSICOLOR EXTRACTS, METHODS OF PREPARATION AND USES THEREOF

CROSS REFERENCE TO A RELATED APPLICATION

This application is a National Stage Application of International Application Number PCT/IB2011/002845, filed Oct. 6, 2011; which claims priority to U.S. Provisional Application No. 61/390,279, filed Oct. 6, 2010 and U.S. Provisional Application No. 61/432,853, filed Jan. 14, 2011; all of which are incorporated herein by reference in their entirety.

BACKGROUND OF THE INVENTION

*Coriolus versicolor*, also known as *Agaricus versicolor, Boletus versicolor, Polyporus versicolor, Polystictus versicolor, Poria versicolor, Trametes versicolor, Yun-Zhi* (Chinese), *Kawaratake* (Japanese), and "turkey tail" (North America), belongs to the Basidiomycetes class and Polyporaccae family. It is widely distributed throughout the world, where more than 120 different strains have been identified in the wooded temperate zones of Asia, Europe, and North America.

The medicinal value of *C. versicolor* was first recorded in *Compendium of Materia Medica* (*Compendium Medica*) by Li Shi Zhen during the Ming Dynasty (1368-1644AD) in China. According to *Compendium Medica, C. versicolor* (Yun-Zhi), if consumed regularly, can invigorate vital energy, maintain one's optimal weight, promote longevity, and avoid unnecessary aging. *C. versicolor* is also believed to have protective effects on liver and spleen function (3), and has been used in the treatment of a variety of symptoms associated with liver dysfunction and respiratory tract infection. In China and Japan, *C. versicolor* is dried, ground, and made into tea. *C. versicolor* has not been reported to have toxic effects in long-term uses (24).

It is reported that *C. versicolor* has immunomodulatory (4), anti-tumor (4), antimicrobial (5) and antiviral effects (6, 7). These pharmacological effects may be largely produced by polysaccharide-peptides (PSP) such as polysaccharide Krestin (PSK) (4).

Specifically, *C. versicolor* is reported to strengthen the immune system that defends against pathogens and diseases. In vitro experiments revealed that aqueous extracts of *C. versicolor* effectively activated immune cells, including T lymphocytes (8-14), B lymphocytes (9, 13), monocytes/macrophages (9, 12, 13, 15), bone marrow cells (13), natural killer cells, and lymphocyte-activated killer cells (8, 9). In addition, it is reported that *C. versicolor* extracts enhance the production of antibodies and various cytokines, including interleukins such as IL-2 and IL-6, interferons, and tumor necrotic factors (9). In vivo studies also demonstrated that aqueous *C. versicolor* extracts help to restore immune responses in patients who received chemotherapy (5, 14, 16, 17) and help to reduce immuno-suppression caused by anticancer drugs.

In addition, *C. versicolor* can inhibit the growth, migration and metastasis of tumor cells (18). Studies have shown that a *C. versicolor* extract inhibits the growth of cancer cells in vitro, including gastric cancer cells (e.g., 7907), lung cancer cells (e.g., SPC), leukemia cells (e.g., MCL), lymphoma cells (e.g., SLY), human leukemia cells (e.g., HK-60), liver cancer cells (e.g., SMMU-7721), and stomach cancer cells (e.g., SCG-7901) (16, 19-23). The extract may also be used for prophylaxis against esophageal, colon, breast, liver, lung, and bladder cancers (9). While the *C. versicolor* extract exhibits potent anti-tumor activity, it has little cytotoxic effects on normal cells (25).

While *C. versicolor* has a long history of empiric uses, there is still limited knowledge about the precise mechanism by which it exerts its pharmacological action. In addition, many biologically-active chemical constituents of *C. versicolor* have not been identified. Thus, a need exists for elucidating the drug mechanism of *C. versicolor*, as a means through which novel therapeutic compositions and methods can be developed. In addition, a need exists for the development of more efficient and convenient extraction protocols for scaling-up the production of *C. versicolor* extracts and for the identification of its biologically-active chemical constituents for therapeutic uses.

BRIEF SUMMARY OF THE INVENTION

The subject invention provides efficient and convenient methods for preparing *C. versicolor* extracts for therapeutic use. In one embodiment, the subject invention provides a method for preparing *C. versicolor* extracts and/or for isolating biologically-active chemical constituents from *C. versicolor*, comprising the steps of:

a) providing a sufficient quantity of raw material of *C. versicolor*;

b) extracting the raw material of *C. versicolor* with a polar solvent at a temperature of about 15° C. to about 30° C. to yield a *C. versicolor* extract and a residue, wherein step b) is performed once or more than once; and c) recovering the *C. versicolor* extract. Preferably, the *C. versicolor* extract comprises biologically-active chemical constituents, including polysaccharide-peptides (PSP) such as polysaccharide Krestin (PSK) or other bioactive small molecules. In one embodiment, the *Coriolus versicolor* extracts can be further evaporated to produce solid or semi-solid compositions.

The subject invention further provides *C. versicolor* extracts produced by the subject extraction methods. Also provided are pharmaceutical compositions comprising a therapeutically effective amount of the subject *C. versicolor* extract and, optionally, a pharmaceutically acceptable carrier. The subject invention also provides dietary supplements and health food or drink formulations comprising the *C. versicolor* extract of the invention.

In a further embodiment, the subject method comprises creating a chemical profile for the *C. versicolor* extract, by using a combination of high performance liquid chromatography (HPLC) and/or gas chromatography-mass spectrometry (GC-MS).

The subject invention also provides methods for preventing, treating or ameliorating a disease or condition where modulation of an immune response is beneficial. In one embodiment, the method comprises administering, to a subject in need of such treatment, an effective amount of a composition comprising a therapeutically effective amount of the *C. versicolor* extract of the subject invention.

In one embodiment, the compositions of the subject invention can be used to treat or ameliorate cancer or tumors including, but not limited to, brain tumors, nasopharyngeal carcinoma, breast cancer, lung cancer, leukemia, lymphoma, colon cancer, liver cancer, stomach cancer, esophageal cancer, bladder cancer, and gastric cancer.

In a preferred embodiment, the subject invention can be used to treat or ameliorate glioblastoma multiforme, nasopharyngeal carcinoma, breast carcinoma, lung carcinoma, prostate cancer, and/or colon carcinoma.

In another embodiment, the subject invention can be used to treat or ameliorate infection by herpes simplex virus (HSV) and related herpes viruses including, but not limited to, varicella zoster, cytomegalovirus, and herpes virus-S. These viral infections are commonly found in cancer or immunocompromised patients.

DETAILED DESCRIPTION OF THE INVENTION

Figure 1A:
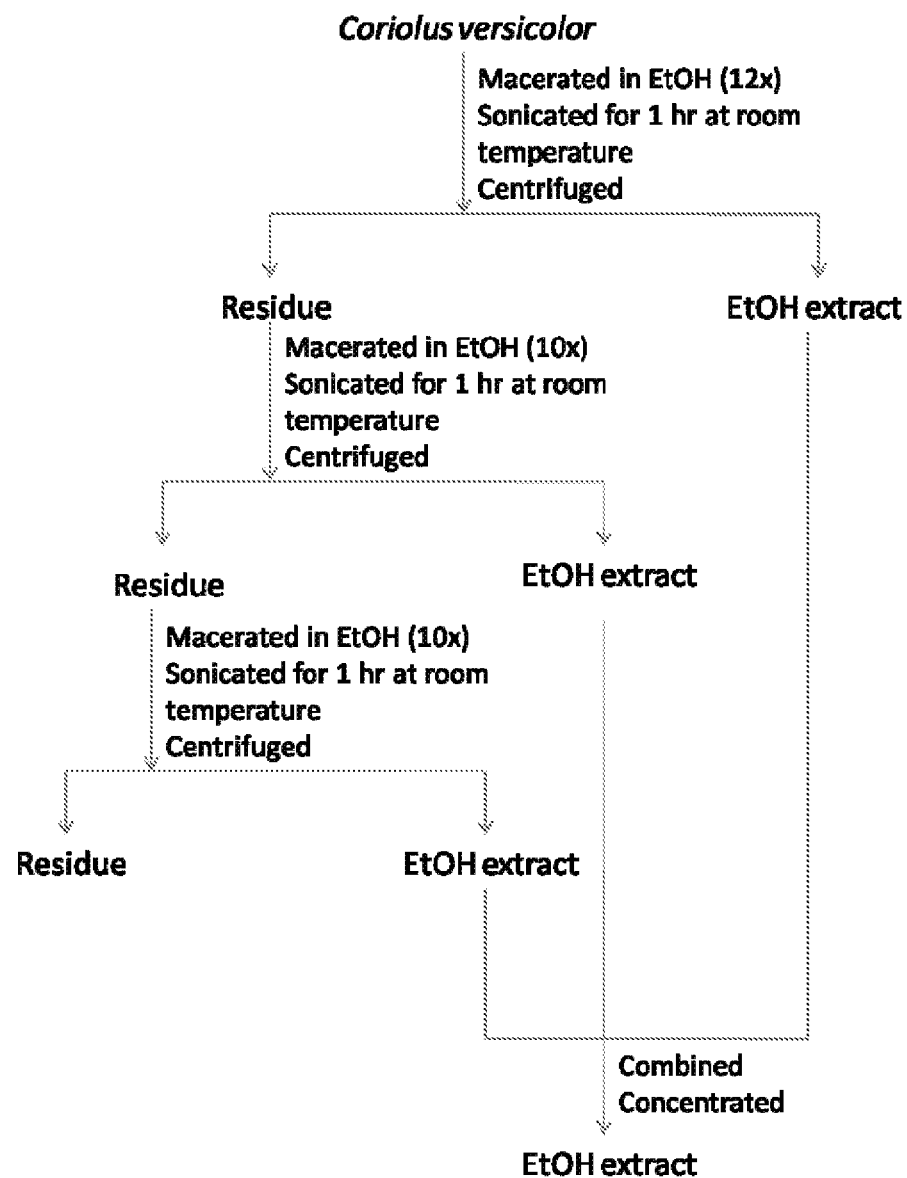
FIGS. 1A-C illustrate exemplified extraction schemes for *Coriolus versicolor*. (A) The ethanol extract of *C. versicolor* was obtained by extracting *C. versicolor* in EtOH (12-fold volume) with continuous sonication for 1 hr at room temperature. Briefly, raw materials of *C. versicolor* were macerated in 12-fold volume of ethanol with continuous sonication for 1 hr. The residues were macerated in 10-fold volume of EtOH and the extraction procedure was repeated twice. The extracts were collected, combined, and evaporated to dryness under vacuum. (B) The *C. versicolor* extract was prepared by sequential extraction, using 12×EtOH as the first solvent at room temperature, 10×50% EtOH as the second solvent under heating conditions, and 10×0.04% NaOH solution as the third solvent under heating conditions. The extracts were collected, combined, concentrated, and lyophilized. (C) The *C. versicolor* extract was prepared by sequential extraction, using 10×50% EtOH as the first solvent, and 10×0.04% NaOH solution as the second solvent. The extraction procedure was performed under heating conditions. The extracts were collected, combined, concentrated, and lyophilized.

The subject invention provides efficient and convenient methods for preparing *Coriolus versicolor* extracts. In one preferred embodiment, the *C. versicolor* extract is prepared at room temperature, using water, ethanol, or a mixture of ethanol-water, as the solvent. In one embodiment, the *C. versicolor* extract can be further evaporated to produce solid or semi-solid compositions.

The subject invention further provides *C. versicolor* extracts produced by the subject extraction methods. Also provided are therapeutic or pharmaceutical compositions comprising a therapeutically effective amount of the subject *C. versicolor* extract and, optionally, a pharmaceutically acceptable carrier. The subject invention also provides dietary supplements and health food or drink formulations comprising the *C. versicolor* extract of the invention.

In a further embodiment, the subject method comprises creating a chemical profile for the *C. versicolor* extract, by using a combination of high performance liquid chromatography (HPLC) and/or gas chromatography-mass spectrometry (GC-MS).

The subject invention also provides methods for preventing, treating or ameliorating a disease or condition where modulation of an immune response is beneficial. In one embodiment, the method comprises administering, to a subject in need of such treatment, an effective amount of a composition comprising the *C. versicolor* extract of the subject invention.

Specifically, the compositions of the subject invention can be used to treat or ameliorate a disease or condition, where the stimulation of IFNβ production and/or a reduction of TNF-α, IL10, and/or MMP-3 production is beneficial.

In a preferred embodiment, the subject invention can be used to treat glioblastoma multiforme and/or nasopharyngeal carcinoma. In another embodiment, the subject invention can be used to treat bacterial, viral, and/or microbial infection. In certain embodiments, the subject invention can be used to treat infections including, but not limited to, varicella zoster, cytomegalovirus, and herpes virus 8 infections, which are common viral infections found in cancer or immunocompromised patients.

*Coriolus versicolor* Extracts

One aspect of the subject invention provides methods for preparing *Coriolus versicolor* extracts. The subject methods can also be used to isolate biologically-active chemical constituents from *C. versicolor*. Also provided are *C. versicolor* extracts prepared in accordance with the subject invention.

In a preferred embodiment, the subject invention provides a method for preparing *C. versicolor* extract and/or for isolating biologically-active chemical constituents from *C. versicolor*, comprising, consisting essentially of, or consisting of the steps of:

a) providing a sufficient quantity of raw material of *C. versicolor*;

b) extracting the raw material of *C. versicolor* with a polar solvent at a temperature of about 15° C. to about 30° C. to yield a *C. versicolor* extract and a residue, wherein step b) is performed once or more than once; and c) recovering the *C. versicolor* extract.

Advantageously, using a polar solvent at a temperature of about 15° C. to about 30° C. facilitates the extraction of one or more biologically-active, small molecule chemical constituents, which have anti-cancer and/or anti-viral effects.

Preferably, the raw material of *C. versicolor* is dried and ground into powder. Preferably, the *C. versicolor* extract comprises biologically-active chemical constituents, including polysaccharide-peptides (PSP) such as polysaccharide Krestin (PSK). Preferably, the raw materials are *C. versicolor* fruit bodies.

In certain embodiments, suitable solvents for the preparation of *C. versicolor* include, but are not limited to, alcohols (e.g., $C_1$-$C_8$ alcohols (e.g. methanol, ethanol, propanol, and butanol; $C_1$-$C_8$ alkyl polyols); $C_1$-$C_8$ ketones (e.g. acetone) or alkyl ketones; chloroform; acetic acid; water; and inorganic acids such as hydrochloric acid. In one embodiment, the subject invention utilizes a ratio of *C. versicolor* to solvent (v/v) of between 1:5 and 1:20, and preferably about 1:10, 1:12, or 1:15. In preferred embodiments, the subject extraction procedure utilizes water, alcohol (e.g., ethanol), or a mixture of alcohol-water (e.g., ethanol-water), as the solvent. The alcohol-water (e.g., ethanol-water) mixture can comprise about 5%, 10%, 15%, 20%, 25%, 30%, 35%, 40%, 50%, 55%, 60%, 65%, 70%, 75%, 80%, 85%, 90%, or 95% alcohol (e.g., ethanol).

It is preferred that step (b) of the extraction procedure is performed at room temperature. Step (b) can also be performed at a temperature slightly below or above room temperature. In one embodiment, step (b) is performed at a temperature of about 15° C. to about 30° C., about 18° C. to about 28° C., about 20° C. to about 28° C., or about 22° C. to about 26° C. In a specific embodiment, step (b) is performed at about 25° C.

In one embodiment, the raw material of *C. versicolor* is macerated in cold solvent, preferably at, or below, room temperature during step (b) of the extraction procedure. In one embodiment, neither the solvent nor the raw material of *C. versicolor* has been boiled or heated to a temperature of higher than 50° C., or higher than 45° C., prior to and/or during step (b) of the extraction procedure.

In one embodiment, the raw material of *C. versicolor* is mixed with solvent for at least about 15 minutes to extract the biologically-active chemical constitutes. Preferably, the extraction time is at least about 20 minutes, 30 minutes, 40 minutes, 50 minutes, 1 hour, 1.5 hours, 2 hours, 2.5 hours, 3 hours, 4 hours, or 5 hours.

Preferably, step (b) of the extraction is performed with continuous sonication. Sonication is a method that can, in some cases, improve the efficiency and shorten the extraction time for extracting compounds from the dry medicinal material. The underlying mechanism of such enhancement is the intensification of mass transfer and easier access of the solvent to the medicinal material. Thus, sonication is an expeditious, inexpensive and efficient alternative to conventional extraction techniques and, in some cases, even superior to supercritical fluid and microwave-assisted extraction.

In preferred embodiments, during step (b), the raw material of *C. versicolor* is mixed with the solvent with continuous sonication for at least about 5 minutes, 10 minutes, 15 minutes, 20 minutes, 30 minutes, 40 minutes, 50 minutes, 1 hour, 1.5 hours, 2 hours, 2.5 hours, 3 hours, 4 hours, or 5 hours. However, it has been found by the present inventors that, in certain instances, sonication may not improve the extraction yield of certain chemical constituents, which can be easily leached out from the raw medicinal materials to the solvent. In such cases, the extraction procedure is preferably performed without, or with little, sonication.

The *C. versicolor* extract can be recovered by, for example, techniques that facilitate the separation of the solid phase (e.g. residues) from the liquid phase containing the solvent extract, such as by centrifugation. The extract can be collected by, for example, filtration to remove the residues. In one embodiment, the *C. versicolor* extract may be further evaporated to produce solid or semi-solid compositions. In another embodiment, the *C. versicolor* extract may be concentrated and/or purified.

The *C. versicolor* extract can be obtained via a single extraction or sequential extraction. In one embodiment, after recovering the first extract, the residues may be re-dissolved in the same solvent for further extraction. In another embodiment, the *C. versicolor* extract can be obtained via sequential extraction, by extracting the solvent-extract or the residues with a different solvent each time to extract the desired biologically-active chemical constituents.

In one embodiment, the extraction method of the subject invention further comprises, consists essentially of, or consists of, after steps (a)-(b), the step of extracting *C. versicolor* residue with a polar solvent under heating conditions (such as at a temperature of about 60° C. or higher) to yield a second *C. versicolor* extract and a second residue.

In another embodiment, the extraction method of the subject invention further comprises, consists essentially of, or consists of, after steps (a)-(b), the step of extracting *C. versicolor* residue with an aqueous alkaline solution (such as NaOH and KOH) under heating conditions (such as at a temperature of about 60° C. or higher) to yield a second *C. versicolor* extract and a second residue. In one embodiment, the aqueous alkaline solution has a normality of 0.1N or any value lower than 0.1N, such as 0.05N, 0.02N, 0.01N, or 0.001N.

In a specific embodiment, the extraction method of the subject invention comprises:

a) providing a sufficient quantity of raw material of *C. versicolor;* b) extracting the raw material of *C. versicolor* with a first polar solvent at a temperature of about 15° C. to about 30° C. to yield a first *C. versicolor* extract and a first residue;

c) extracting the first residue with a second polar solvent under heating conditions (such as at a temperature of about 60° C. or higher), to yield a second *C. versicolor* extract and a second residue: and d) extracting the second residue with an alkaline solution under heating conditions (such as at a temperature of about 60° C. or higher), to yield a third *C. versicolor* extract and a third residue; and e) recovering the *C. versicolor* extracts.

In another specific embodiment, the extraction method of the subject invention comprises:

a) providing a sufficient quantity of raw material of *C. versicolor;* b) extracting the raw material of *C. versicolor* with a first polar solvent under heating conditions (such as at a temperature of about 60° C. or higher), to yield a first *C. versicolor* extract and a first residue; and c) extracting the first residue with an alkaline solution (such as NaOH and KOH) under heating conditions (such as at a temperature of about 60° C. or higher), to yield a second *C. versicolor* extract and a second residue; and d) extracting the *C. versicolor* extracts.

In one embodiment, the extraction method of the subject invention comprises, consists essentially of, or consists of:

a) providing a sufficient quantity of raw material of *Coriolus versicolor;* b) extracting the raw material of *Coriolus versicolor* with a polar solvent to yield a *Coriolus versicolor* extract and a residue, and recovering the *Coriolus versicolor* extract, wherein step b) is performed once or more than once;

c) extracting the residue obtained in step b) with an aqueous alkaline solution to yield an aqueous extract, and recovering the aqueous extract, wherein step c) is performed once or more than once; and d) combining one or more extracts obtained from step b) and c) to yield a *Coriolus versicolor* extract.

In certain embodiments, the polar solvent used to extract *C. versicolor* under heating conditions comprises a $C_1$-$C_8$ alcohol (e.g. methanol, ethanol, propanol, and butanol). In a specific embodiment, the polar solvent used to extract *C. versicolor* under heating conditions is ethanol or ethanol-water mixture. In a specific embodiment, the polar solvent used to extract *C. versicolor* under heating conditions is not water.

According to the subject invention, heating can be performed at a temperature of higher than 60° C., higher than 65° C., higher than 70° C., higher than 75° C., higher than 80° C., higher than 85° C., higher than 90° C., higher than 95° C., or higher than 100° C.

Figure 1B:
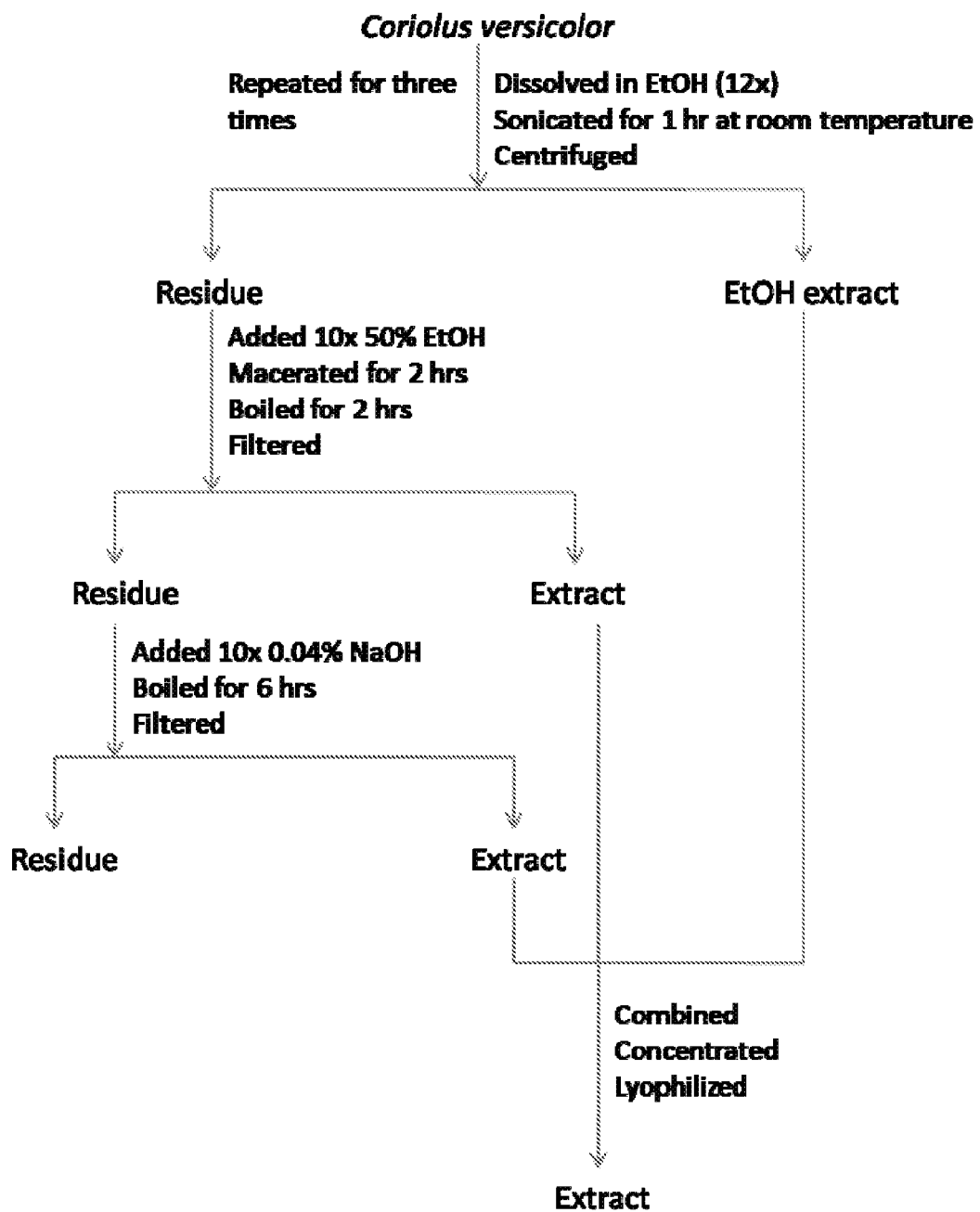
Figure 1C:
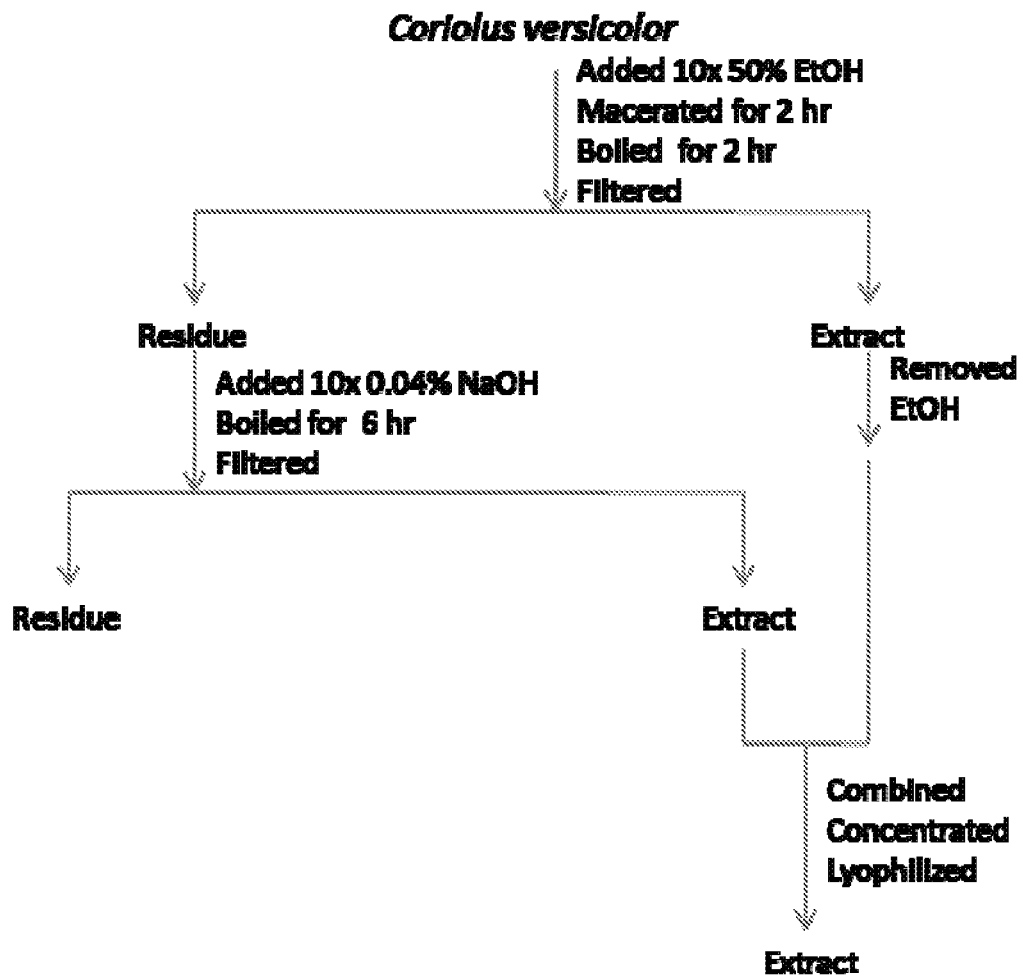

FIGS. 1A-C illustrate preferred embodiments of the extraction method of the subject invention.

Advantageously, using alkaline solution as a solvent facilitates the extraction of biologically-active, large-molecule chemical constituents, including polysaccharide-peptides (PSP) such as polysaccharide Krestin (PSK).

Figure 4:
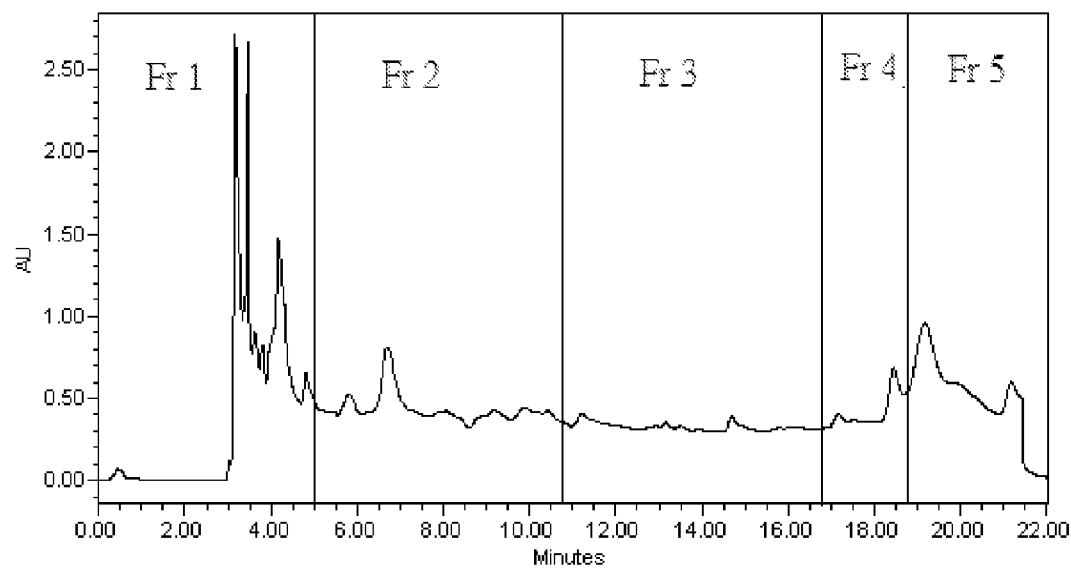
FIG. 4 shows HPLC chromatogram of *C. versicolor* ethanol extract (MPUB-EtOH) prepared using the extraction scheme as shown in FIG. 1A. The extract of MPUB-EtOH was further separated into 5 fractions using a reversed-phase column (Lichrospher 100 RP C18, EC 5 um). The flow rate was set at 1.0 ml/min and the water-acetonitrile mixture was used as the mobile phase. Peaks were detected at 210, 254, and 280 nm.

In a further embodiment, the *C. versicolor* crude extract can be fractionated or separated to yield one or more fractions that contain the desired biologically-active chemical constituents. In one embodiment, the *C. versicolor* crude extract is subject to HPLC using water-acetonitrile as the mobile phase. In a specific embodiment, the *C. versicolor* crude extract is subject to HPLC using the elution parameters illustrated in Table 1, thereby yielding 5 fractions as shown in FIG. 4.

In a further embodiment, the subject method comprises creating a chemical profile for the *C. versicolor* extract, by using a combination of HPLC and/or gas chromatography-mass spectrometry (GC-MS). In one embodiment, the method comprises: subjecting the extract to a HPLC, eluting the extract, and creating a chemical profile for the extract following HPLC. In another embodiment, the method comprises: subjecting the extract to a gas chromatography-mass spectrometry and creating a chromatographic/spectrometric profile for the extract.

Figure 2A:
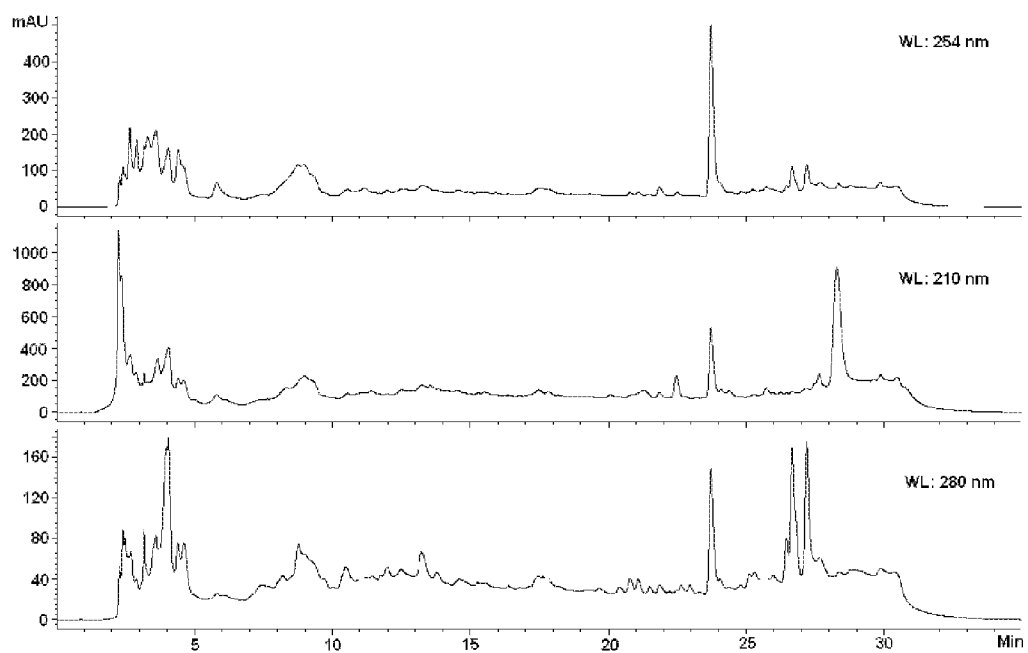
FIGS. 2A-C show high performance liquid chromatography (HPLC) chromatograms of *C. versicolor* ethanol extract prepared using the extraction schemes as shown in FIGS. 1A, 1B, or by macerating the raw materials of *C. versicolor* in ethanol for 18 hrs. The *C. versicolor* ethanol extract was subject to HPLC by using Agilent 1200 series HPLC system with a column packed with ODS-bonded silica gel (Lichrospher 100 RP C18, EC 5 um). The flow rate was set at 1.0 ml/min and the water-acetonitrile mixture was used as the mobile phase. Peaks were detected at 210, 254, and 280 nm. (A) HPLC chromatograms of *C. versicolor* extract, which was extracted with ethanol under continuous sonication for 1 hr. The extraction procedure was repeated twice. (B) HPLC chromatograms of *C. versicolor* extract, which was extracted by maceration in ethanol for 18 hrs. (C) HPLC chromatograms of *C. versicolor* extract, which was extracted using the extraction scheme as shown in FIG. 1B. Briefly, *C. versicolor* was extracted with ethanol at room temperature and then extracted with 50% ethanol under heating conditions.
Figure 2B:
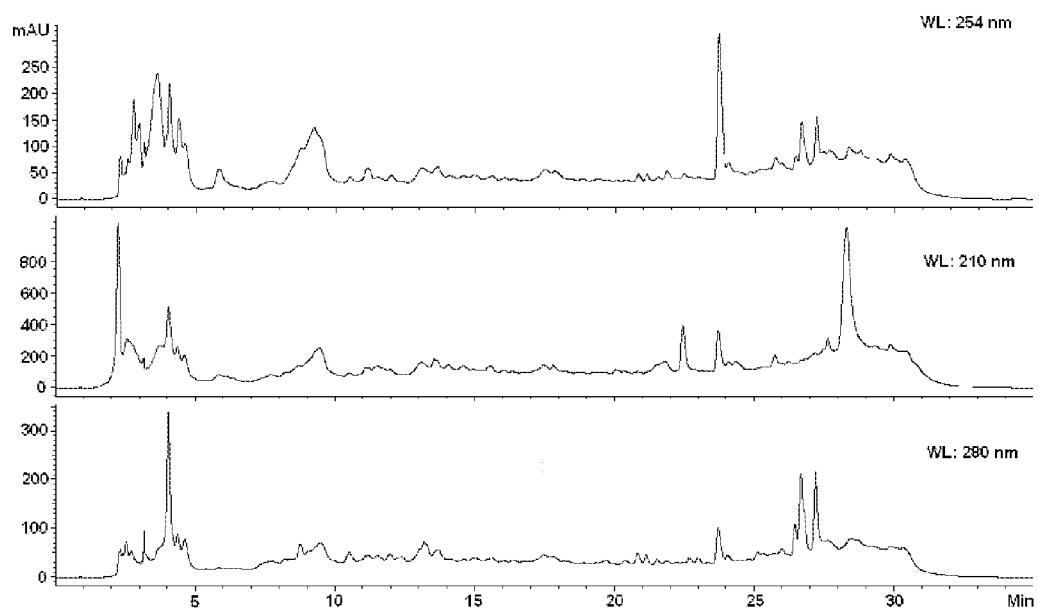
Figure 2C:
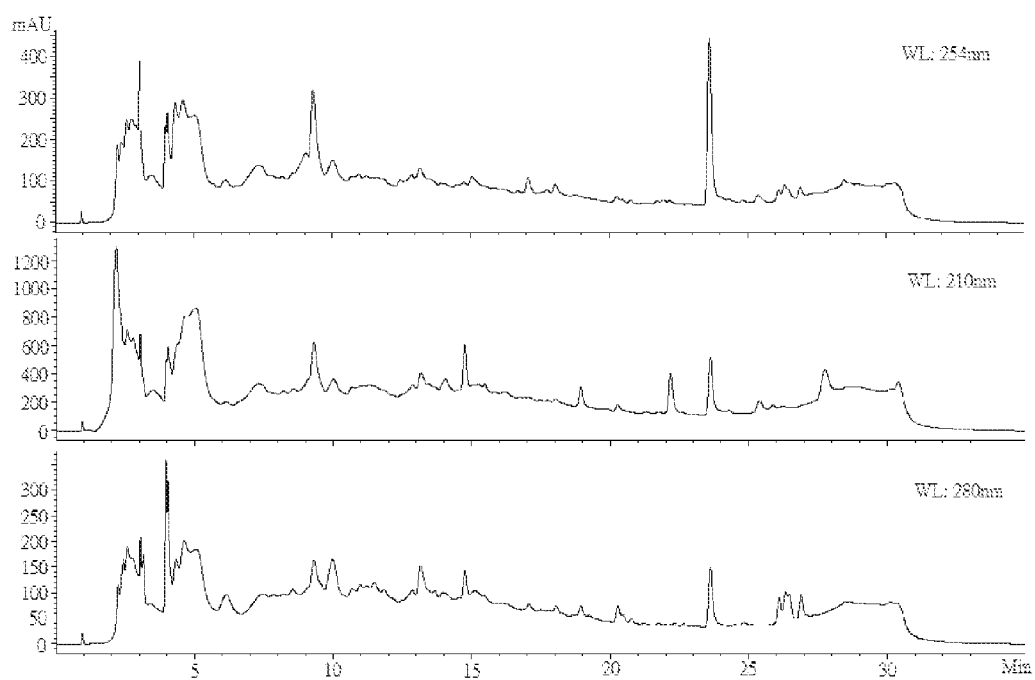
Figure 3A:
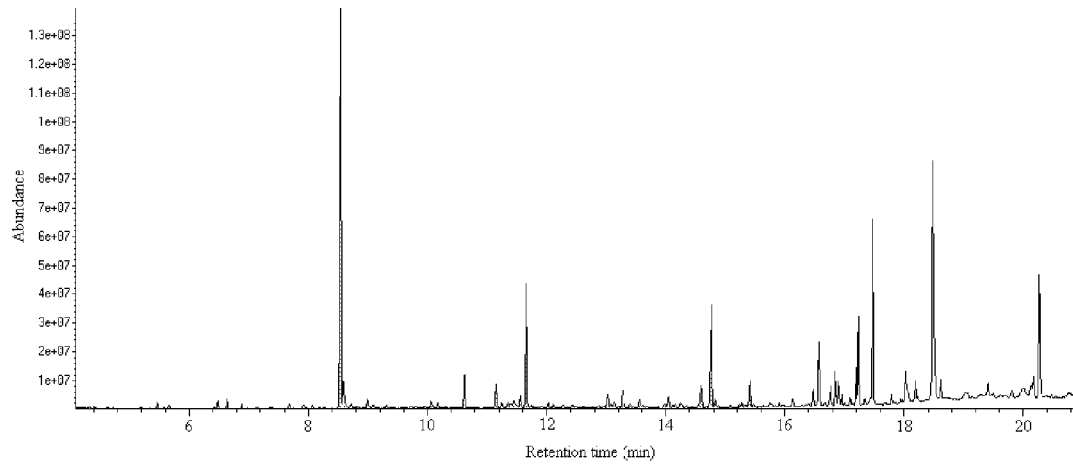
FIG. 3A-B show gas chromatography (GC) total ion chromatogram of *C. versicolor* ethanol extract prepared using the extraction scheme as shown in FIG. 1A or by macerating the raw materials of *C. versicolor* in ethanol for 18 hrs. The extract was mixed with pyridine and a derivatizing agent BSTFA [N,O-bis(trimethylsilyl)trifloroacetamide] at 70° C. for 2 hrs. The resulting mixture was analyzed by gas chromatography mass spectrometry (GC-MS) with a HP-5MS column (30 m×250 um×0.25 um). The initial oven temperature was maintained at 70° C. for 1 min, increased to 180° C. at a rate of 10° C. per min, maintained at 180° C. for 2 min, increased to 280° C. at a rate of 10° C. per min, and maintained at 280° C. for 3 min. The injector temperature was set at 275° C. Helium at a flow rate of 1 ml/min was used as the carrier gas. (A) Gas chromatography (GC) total ion chromatogram of *C. versicolor* extract, which was extracted with ethanol under continuous sonication for 1 hr. The extraction procedure was repeated twice. (B) Gas chromatography (GC) total ion chromatogram of *C. versicolor* extract, which was extracted by maceration in ethanol for 18 hrs.
Figure 3B:
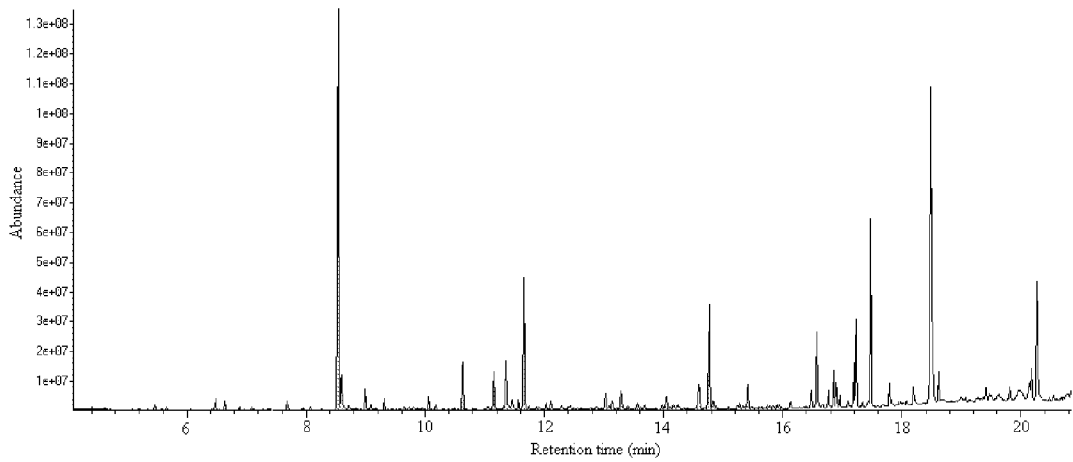

The subject invention further provides *C. versicolor* extracts produced by the subject extraction methods. In a specific embodiment, the *C. versicolor* extract has a high performance liquid chromatography (HPLC) profile as shown in FIGS. 2A, 2B, 2C, or any of Fractions 1-5 as shown in FIG. 4; and/or a gas chromatography-mass spectrometry (GC-MS) profile as shown in FIG. 3A or 3B.

The term "consisting essentially of," as used herein, limits the scope of the invention to the specified steps and those that do not materially affect the basic and novel characteristic(s) of the subject invention, i.e., a method for preparing *C. versicolor* extract and/or for isolating biologically-active chemical constituents from *C. versicolor*. For instance, by using "consisting essentially of," the method for preparing *C. versicolor* extract does not contain any unspecified steps of extracting or contacting *C. versicolor*, for example, additional step(s) of extracting or contacting *C. versicolor* with unspecified solvent(s), or extracting *C. versicolor* under condition(s) (e.g., temperature) different from the specified condition. Also, by using the term "consisting essentially of," the process may comprise steps that do not materially affect the extraction of biologically-active chemical constituents from *C. versicolor* including collecting or recovering the *C. versicolor* extract; concentrating the *C. versicolor* extract; combining multiple *C. versicolor* extracts into a single composition; lyophilizing or drying the *C. versicolor* extract into a solid or semi-solid composition; formulating the *C. versicolor* extract into a pharmaceutical composition such as solutions, suspensions, tablets, capsules, granules, powders, decoctions, and tinctures; mixing the *C. versicolor* extract with pharmaceutically-acceptable carriers, excipients, flavoring agents, buffering agents, and/or emulsifying agents; and packaging the *C. versicolor* extract.

Modulation of Immune Responses

Another aspect of the subject invention provides therapeutic uses of the *Coriolus versicolor* extracts for modulating immune responses. Advantageously, the *C. versicolor* extracts of the subject invention stimulate protective immune responses while suppressing unwanted immune responses that can cause disease. For instance, the *C. versicolor* extracts can restore or improve depressed immune system function, which is caused by, for example, the administration of anti-cancer agents. In another embodiment, the *C. versicolor* extracts can stimulate protective immune responses that defend against viral, bacterial, and/or microbial infection. In addition, the *C. versicolor* extracts of the subject invention can suppress unwanted immune responses, such as the production of TNF-α and its induction of metalloproteinase production, which are utilized by certain tumor cells to promote metastasis.

Specifically, it is now discovered by the present inventors that *C. versicolor* reduces the production of TNF-α, a pro-inflammatory mediator that plays a critical role in the acute-phase immune response against pathogenic infection and tumorigenesis. TNF-α also induces the production of matrix metalloproteinases (MMPs) and MMP family members, which degrade extracellular matrix proteins. However, certain tumor cells (such as glioblastomas, nasopharyngeal carcinomas, breast carcinoma, lung carcinoma, prostate cancer, and colon carcinoma) have developed resistance to the cytotoxic effects of TNF-α. As a result, these tumor cells utilize the induction of MMP by TNF-α to invade neighboring tissues as well as organs located in distant parts of the body.

Advantageously, *C. versicolor* inhibits TNF-α production in tumor cells and, thus, is particularly useful for preventing or reducing the metastatic spread of malignant tumor cells (such as glioblastoma, nasopharyngeal carcinoma, breast carcinoma, lung carcinoma, prostate cancer cells, and colon carcinoma) that are resistant to TNF-α.

In addition, it is now discovered by the present inventors that *C. versicolor* reduces the production of IL-10, an anti-inflammatory cytokine that down-regulates the expression of pro-inflammatory cytokines. It is also discovered by the present inventors that *C. versicolor* enhances the production of IFN-β, which stimulates the acute-phase immune response against pathogenic invasion.

In one embodiment, the subject invention provides a method for preventing, treating, or ameliorating a disease or condition where modulation of immune responses would be beneficial. The method comprises administering, to a subject in need of such treatment, an effective amount of a composition comprising the *C. versicolor* extract of the subject invention. Specifically, the compositions of the subject invention can be used to treat or ameliorate a disease or condition, where the stimulation of IFNβ production and/or reduction of TNF-α and/or IL-10 production would be beneficial.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, cats, horses, cattle, pigs, sheep, goats, chickens; and other animals such as mice, rats, guinea pigs, and hamsters.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence f symptoms.

The term "effective amount," as used herein, refers to an amount that is capable of treating or ameliorating a disease or condition or otherwise capable of producing an intended therapeutic effect. In certain embodiments, the effective amount enables at least 5%, 10%, 15%, 20%, 25%, 30%, 35%, 40%, 45%, 50%, 60%, 70%, 80%, 90%, or 100% reduction in TNF-α and/or IL-10 production. In certain embodiments, the effective amount enables at least 5%, 10%, 15%, 20%, 25%, 30%, 35%, 40%, 45%, 50%, 60%, 70%, 80%, 90%, or 100% increase in IFNβ production.

In one embodiment, the compositions of the subject invention can be used to treat or ameliorate cancer or tumors including, but not limited to, brain tumors, nasopharyngeal carcinoma, breast cancer, leukemia, lymphoma, colon cancer, liver cancer, stomach cancer, esophageal cancer, bladder cancer, and gastric cancer.

In a preferred embodiment, the subject invention can be used to prevent or reduce the metastatic spread of tumor cells, particularly those tumor cells that become resistant to the cytotoxic effects of TNF-α. In a specific embodiment, the subject invention can be used to treat glioblastoma multiforme, breast carcinoma, lung carcinoma, prostate cancer, colon carcinoma and/or nasopharyngeal carcinoma. In a further specific embodiment, the subject invention can be used to prevent or reduce the metastatic spread of glioblastoma multiforme, breast carcinoma, lung carcinoma, prostate cancer, colon carcinoma, and/or nasopharyngeal carcinoma.

In one embodiment, the subject invention can be used to strengthen the immune system and/or restore or improve immune system function. In a specific embodiment, the compositions of the subject invention can be used to treat or ameliorate the immuno-suppressive effects of chemotherapy and/or radiation therapy. In one embodiment, the composition of the subject invention is administered before, during, and/or after the administration of a chemotherapeutic agent to counteract the depressive effects of the chemotherapeutic agent on the immune system.

In addition, the compositions of the subject invention can be used to prevent, treat or ameliorate bacterial, viral, fungal, protozoan, and/or other microbial or pathogenic infections. Advantageously, the compositions of the subject invention modulate and/or strengthen immune system function in response to pathogenic infection.

In one embodiment, the compositions of the subject invention can be used to treat or ameliorate viral infection, such as for example, infection by human immunodeficiency virus (HIV), influenza A virus, influenza B virus, hepatitis A virus, hepatitis B virus, hepatitis C virus, herpes simplex virus (HSV), varicella zoster (shingles), herpes virus-8, cytomegalovirus, human T-lymphotropic virus Type I (HTLV-1), bovine leukemia virus (BLV), Epstein-Barr virus, and coronavirus.

In certain embodiments, the compositions of the subject invention can be used to treat or ameliorate fungal infections including, but not limited to, infection by *Candida* and *Aspergillus* species; bacterial infections including, but not limited to, infection by mycobacteria (such as *M. tuberculosis*), *Staphylococcus aureus, Streptococcus pyogenes, Streptococcus pneumoniae, Escherichii coli, Listeria monocytogenes*, and *L. amazonensis*; and protozoan infections including, but not limited to, infection by *Pneumocystis* and *Toxoplasma* species.

In one embodiment, the compositions of the subject invention can be used to treat liver dysfunction, respiratory tract infection, and bronchitis.

Therapeutic Compositions and Formulations

The subject invention provides for therapeutic or pharmaceutical compositions comprising a therapeutically effective amount of the *Coriolus versicolor* extract of the subject invention and, optionally, a pharmaceutically acceptable carrier. The subject invention also provides therapeutic or pharmaceutical compositions comprising biologically-active compounds or chemical constituents isolated from *C. versicolor* in accordance with the subject invention. The present invention also embodies dietary supplements and health food or drink formulations comprising the *C. versicolor* extract of the invention.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, granules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

The therapeutic or pharmaceutical compositions of the invention can be formulated as neutral or salt forms. Pharmaceutically acceptable salts include, but are not limited to, salts formed with hydrochloric, phosphoric, acetic, oxalic, tartaric acids, sodium, potassium, ammonium, calcium, ferric hydroxides, etc.

The invention also provides a pharmaceutical pack or kit comprising one or more containers filled with one or more of the ingredients, e.g., compound, carrier, of the pharmaceutical compositions of the invention.

The compositions of the subject invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in hooks and commonly used by practitioners of herbal medicine.

A tincture is prepared by suspending raw medicinal materials (e.g. herbs and fungus) in a solution of alcohol, such as, for example, wine or liquor. After a period of suspension, the liquid (the alcohol solution) may be administered, for example, two or three times a day, one teaspoon each time.

An extract is a concentrated preparation of the essential constituents of a medicinal raw material. Typically, the essential constituents are extracted from the raw medicinal materials (e.g. herbs and fungus) by suspending the raw medicinal materials in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extractum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Routes of Administration

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In preferred embodiments, the compounds and compositions of the subject invention are administered to a subject by oral administration.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg.

For instance, suitable unit dosages may be between about 0.01 to about 500 mg, about 0.01 to about 400 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg about, 0.01 to about 1 mg, or about 0.01 to about 0.5 mg. Such a unit dose may be administered more than once a day, e.g. two or three times a day.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Materials and Methods

Cell Cultures for Bioassays

Primary human blood macrophages and human leukemic monocyte lymphoma cells (U937) were used in bioassays examining the effects of *C. versicolor* extract on the immune system. Blood mononuclear cells were isolated from blood samples of healthy donors (Hong Kong Red Cross Blood Transfusion Service) by Ficoll-Paque centrifugation and purified by the adherence method as described previously (27-28).

Briefly, blood samples were centrifuged at 3000 rpm for 15 min and were separated into plasma and cell layers. The cell layer was diluted with phosphate buffered saline (PBS) in a ratio of 1:1. The diluted cells were slowly overlaid on Ficoll (GE Healthcare) and centrifuged at 2300 rpm for 20 min for separation of mononuclear cells from erythrocytes. The mononuclear cell layer was removed and washed with RPMI 1640 medium (Gibco) until the supernatant was clear.

The cell pellet was resuspended in RPMI 1640 supplemented with 5% autologous plasma, 1% penicillin and streptomycin (Gibco). The suspension was plated onto a petri dish and incubated at 37° C. for 1 h for monocyte adherence. Following washings with RPMI 1640 and overnight incubation, the adherent monocytes were detached by cold RPMI 1640 containing 5 mM EDTA.

The monocytes were seeded onto 24-well tissue culture plates at a density of $0.5 \times 10^6$ cells/well and incubated with RPMI 1640 supplemented with 5% autologous plasma, 1% penicillin and streptomycin. Differentiated macrophages were obtained after 14 days of in vitro culture as described in our previous reports (27, 30).

Mouse macrophages (RAW 264.7) and human neuroblast cells (SKNSH) obtained from American Type Culture Collection were maintained in cultures for use in nitric oxide assays and herpes simplex virus infection assays, respectively.

Real-Time Reverse Transcription-Polymerase Chain Reaction for Analysis of mRNA

Total RNA extraction was performed by using TRIzol reagent (Invitrogen) according to the manufacturer's instructions. Total RNA was treated with DNase and then reverse transcribed by Superscript II reverse transcriptase (Invitrogen) with oligo (dT) primers. The mRNA levels of cytokines were assayed by using TaqMan gene expression assays (Applied Biosystems) as described in our previous reports (27-30).

Enzyme-Linked Immunosorbent Assay for Analysis of Cytokines

Protein levels of cytokines in the cell culture supernatants were measured by enzyme-linked immunosorbent assay (ELISA) using commercially available assay kits (R&D Systems) (27-30). Each sample was assayed in duplicates.

EXAMPLES

Following are examples that illustrate procedures for practicing the invention. These examples should not be construed as limiting.

Example 1—Preparation of *Coriolus Versicolor* Extract

This Example illustrates preferred extraction schemes for preparing *C. versicolor* extracts.

FIG. 1A illustrates one embodiment of the extraction scheme. Briefly, raw materials of *C. versicolor* were macerated in 12-fold volume of EtOH, extracted for 1 hr with continuous sonication at room temperature, and centrifuged to yield ethanol extract and residues. The residues were macerated in 10-fold volume of EtOH and the extraction procedure was repeated twice as shown in FIG. 1A. The extracts were collected, combined, and evaporated to dryness under vacuum to produce granules comprising *C. versicolor* ethanol extract.

In an embodiment, raw materials of *C. versicolor* were macerated in ethanol for 18 hrs, and centrifuged to yield the ethanol extract and residues.

In an embodiment, milli-Q water is used as the solvent for preparing *C. versicolor* water extract. Briefly, raw materials of *C. versicolor* were macerated in 15-fold volume of milli-Q water, extracted for 30 min with continuous sonication at room temperature, and centrifuged to yield water extract and residues. The residues were re-dissolved in 10-fold volume of water and the extraction procedure was repeated twice. The water extract was collected, combined and evaporated to dryness under vacuum to produce granules comprising *C. versicolor* water extract.

In order to facilitate the extraction of bioactive large molecules, including polysaccharide-peptides (PSP) such as PSK and other bioactive small molecules, raw materials of *C. versicolor* or *C. versicolor* residues were further extracted with alkaline solution (e.g., NaOH, KOH).

FIG. 1B shows another embodiment of the extraction scheme. Briefly, raw materials of *C. versicolor* were macerated in 12-fold volume of ethanol with continuous sonication for 1 hr at room temperature. After centrifugation, the first extract and the first residue were obtained. This procedure was repeated twice. The first residue was macerated in 10-fold volume of 50% ethanol for 2 hrs at room temperature. The ethanol-macerated residue was then boiled for another 2 hrs. Insoluble substances were separated from supernatant by filtration, to yield a second residue and a second extract. The second residue was added into 10×0.04% NaOH and boiled for 6 hrs. Insoluble substances were separated from supernatant by filtration, to yield a third residue and a third extract. The extracts were collected, combined, and lyophilized.

FIG. 1C shows another embodiment of the extraction scheme. Briefly, raw materials of *C. versicolor* were macerated in 10-fold 50% ethanol for 2 hrs at room temperature.

The ethanol-macerated *C. versicolor* raw material was boiled for another 2 hrs. Insoluble substances were separated from supernatant by filtration, to yield a first residue and a first extract. The first residue was added into 10×0.04% NaOH and boiled for another 6 hrs. Insoluble substances were separated from supernatant by filtration, to yield a second residue and a second extract. The extracts were collected, combined, and lyophilized.

Example 2—High Performance Liquid Chromatography Analysis of *Coriolus Versicolor* Extract This Example analyzes the chemical fingerprints of the *C. versicolor* extract by high performance liquid chromatography (HPLC). The *C. versicolor* extract was obtained using the extraction schemes illustrated in FIGS. 1A, 1B, or by macerating the raw material of *C. versicolor* in ethanol for 18 hrs.

Briefly, one hundred ug/uL of the EtOH extract was subject to high performance liquid chromatography (HPLC) analysis using an Agilent 1200 series HPLC system (Binary Pump SL, G1312B) equipped with a PDA detector (G1315C) and an autosampler (G1367C). The chromatographic column (4.6×250 mm) was packed with ODS-bonded silica gel (Lichrospher 100 RP C18, EC 5 um), and the column temperature was maintained at room temperature during the separation.

Five microliters of the *C. versicolor* extract was injected into the HPLC system. HPLC was performed at a flow rate of 1.0 ml/min using a mixture of water and acetonitrile as the mobile phase. Gradient elution methodology was adopted as illustrated in Table 1. Peak detection was achieved using an Agilent 1200 series of fast scanning photodiode array detector set at 210, 254, and 280 nm. FIGS. 2A-C show the chemical profile of the *C. versicolor* ethanol extract following HPLC.

TABLE 1

HPLC Gradient elution profile applied for fingerprint analysis of the *C. versicolor* extracts obtained using the extraction schemes of FIGS. 1A and 1B

| Time (min) | Water | Acetonitrile | Elution |
|---|---|---|---|
| 0-2 | 95 | 5 | Isocratic |
| 2-25 | 95→10 | 5→90 | Linear gradient |
| 25-27 | 10 | 90 | Isocratic |
| 27-30 | 10→95 | 90→5 | Linear gradient |
| 30-35 | 95 | 5 | Isocratic |

Example 3—Gas Chromatography-Mass Spectrometry Analysis of *Coriolus Versicolor* Extract This Example further analyzes the chemical fingerprints of the *C. versicolor* extract by gas chromatography-mass spectrometry (GC-MS). The *C. versicolor* extract was obtained using the extraction scheme illustrated in FIG. 1A or by macerating the raw material of *C. versicolor* in ethanol for 18 hrs.

The *C. versicolor* extract was subjected to silylation before analysis by GC-MS. In brief, 100 ul of the extract (30 ug/μL) in acetonitrile was transferred to a 1 ml reaction vial (Alltech), followed by the addition of 50 ul of pyridine and 50 ul of a derivatizing agent BSTFA [N,O-bis(trimethylsilyl) trifloroacetamide], which reacts with a wide range of polar compounds, thereby replacing labile hydrogen atoms of the polar compounds with a —Si(CH$_3$)$_3$ group. After incubation at 70° C. for 2 hrs, the mixture was ready for GC-MS analysis.

The mixture was analyzed by GC-MS using (GC: Agilent, 7890A; MS: Agilent, 5975C) and a HP-5MS column (30 m×250 um×0.25 um). Helium with a split ratio of 1:50 was used as the carrier gas, and 1 ul helium at a flow rate of 1 ml/min was injected into the column. The initial oven temperature was 70° C., which was maintained for 1 min, increased to 180° C. at a rate of 10° C. per min, maintained at 180° C. for 2 min, increased to 280° C. at a rate of 10° C. per min, and maintained at 280° C. for 3 min. The injector temperature was 275° C.; the interface temperature was 250° C., the ion source temperature was 230° C., and the electron impact ionization (EI) was performed at 200 eV. Mass spectra were analyzed in the range of 50-700 atom mass units (amu) for a run time of 22 min, and the data was processed using Agilent G 1701 EA chemstation. FIG. 3 shows the chromatographic profile of the *C. versicolor* ethanol extracts following GC-MS analysis.

Example 4—Fractionation of *C. Versicolor* Extract

The *C. versicolor* ethanol extract (MPUB-EtOH) obtained using the extraction scheme illustrated in FIG. 1A was further separated into 5 fractions (FIG. 4), using a Waters preparative liquid chromatography system that was equipped with a 1525 binary HPLC pump, a 2998 photodiode array detector and a Waters fraction collector III. The fractionation was performed using a reversed-phase column (Lichrospher 100 RP C18, EC 5um), and the detection wavelength was set at 210, 254 and 280 nm. The gradient program consisted of two solvents (A) water and (B) acetonitrile at a flow of 1 ml/min as follows: 0-16 min, 10-90% B; 16-18 min, 90% B and 18-22 min, 10% B.

Example 5—Effects of *Coriolus Versicolor* Extract on Cytokine Production

Figure 5A:
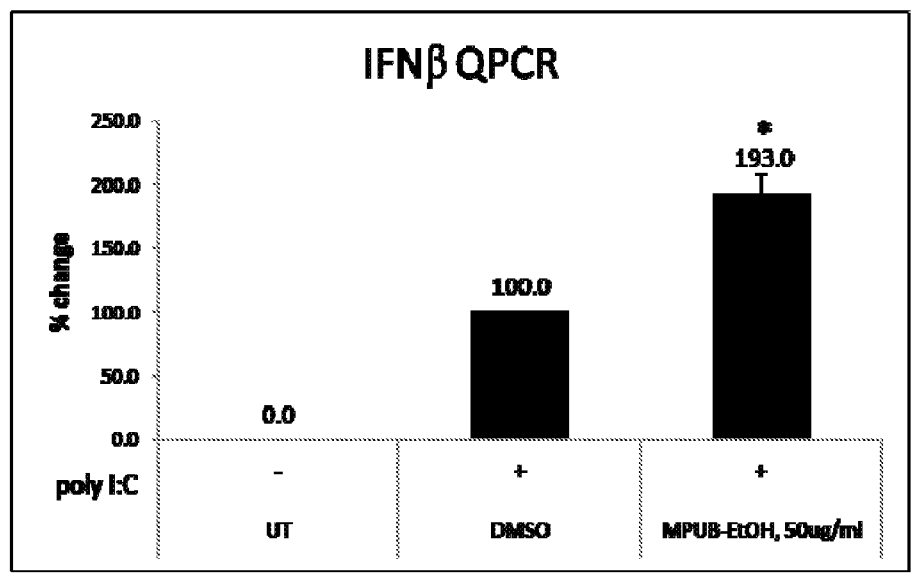
FIGS. 5A-B show that *C. versicolor* extract (MPUB-EtOH) increased. INFβ production (A) and reduced IL10 production (B) in primary human blood macrophages treated with polyinosine-polycytidylic acid (poly(I:C)). All data were plotted as mean values±SD of at least 3 independent experiments. A p value of <0.05 (*) or <0.001 (**) was considered statistically significant.
Figure 5B:
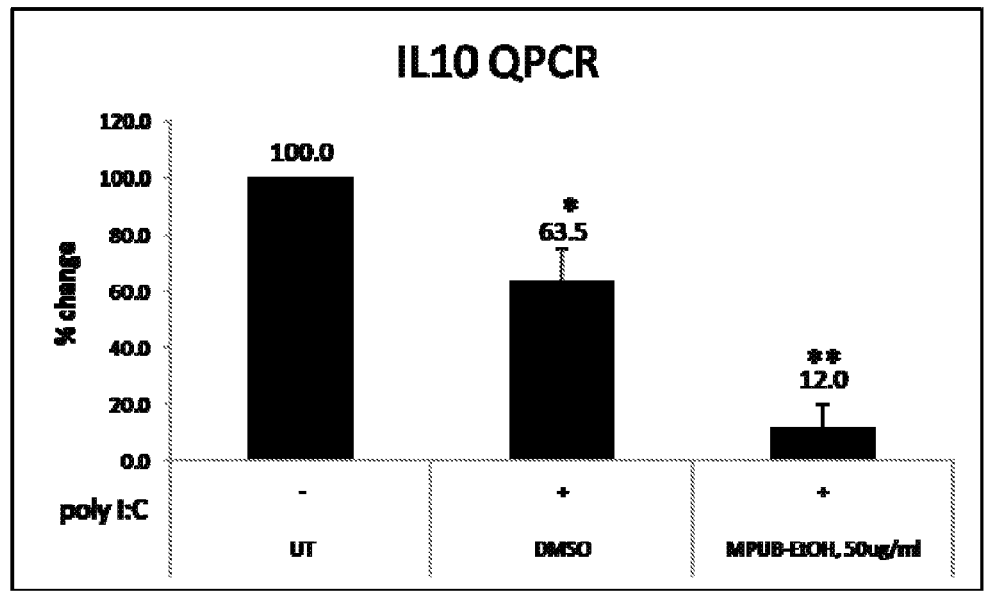

To investigate the effect of *C. versicolor* extract (MPUB-EtOH) on IFNβ and IL-10 production, primary human blood macrophages were pretreated with MPUB-EtOH at 50 ug/ml for 18 hrs. The cells were then treated with polyinosine-polycytidylic acid (poly I:C) (50 ug/ml) for 3 hrs. IFNβ mRNA and IL-10 mRNA levels were analyzed by TaqMan Gene Expression Assays. As shown in FIGS. 5A-B, the *C. versicolor* extract increased IFNβ production and inhibited IL-10 production.

Figure 6A:
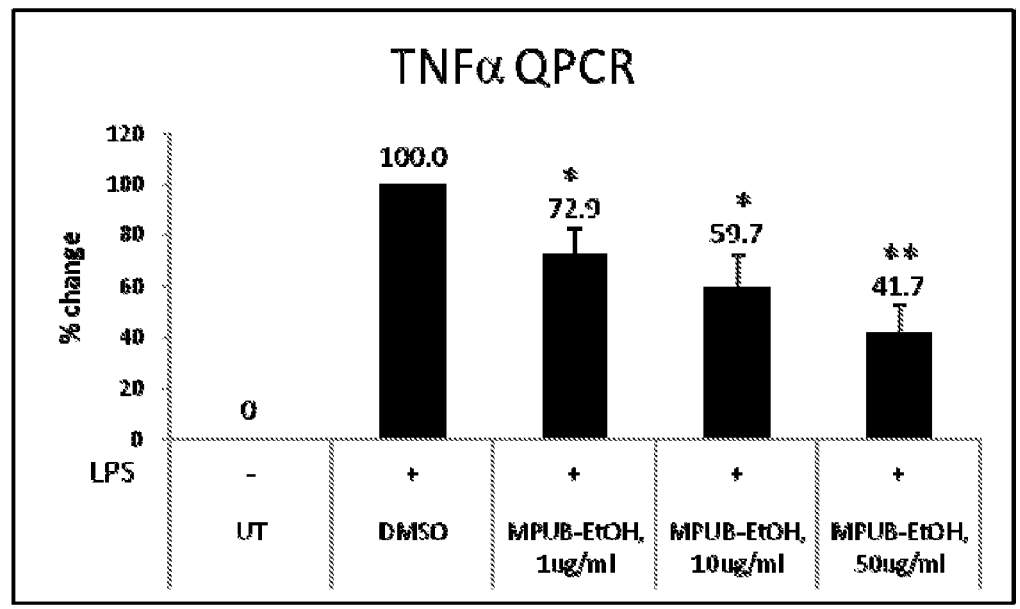
FIGS. 6A-B show that *C. versicolor* extract (MPUB-EtOH) reduced LPS-induced TNFα production. All data were plotted as mean values SD of at least 3 independent experiments. A p value of <0.05 (*) or <0.001 (**) was considered statistically significant.
Figure 6B:
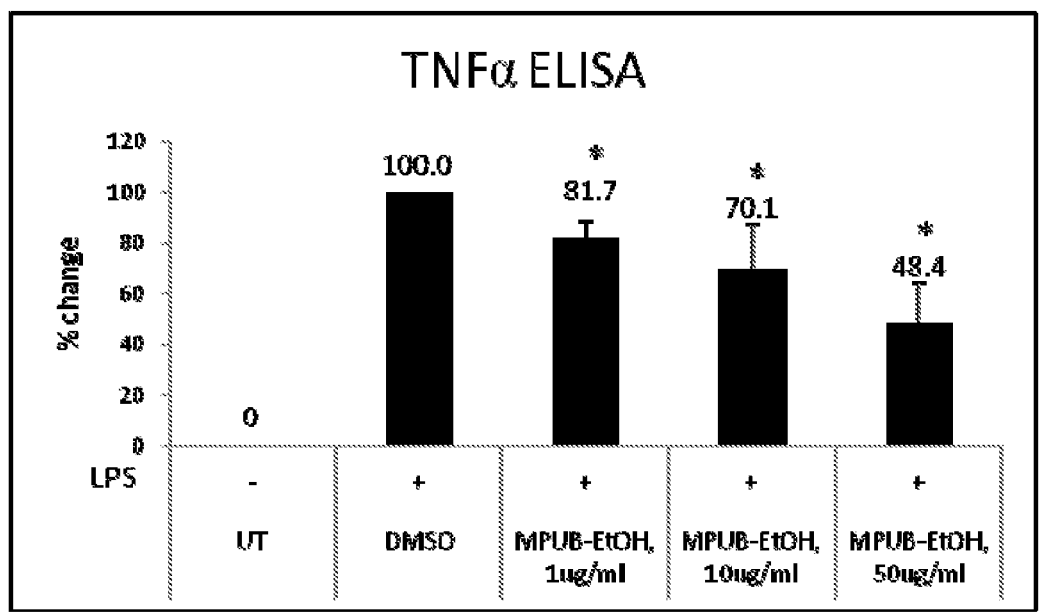

To investigate the effect of *C. versicolor* extract (MPUB-EtOH) on LPS-induced TNFα production, primary human blood macrophages were pretreated with MPUB-EtOH at various concentrations (1, 10 and 50 ug/ml) for 18 hrs. The cells were then treated with lipopolysaccharides (LPS) (1 ng/ml) for 3 and 24 hrs. TNFα mRNA levels and protein levels were analyzed by TaqMan Gene Expression Assays and enzyme-linked immunosorbent assays (ELISA), respectively. As shown in FIGS. 6A-B, *C. versicolor* extract reduced TNFα production in a dose-dependent manner.

Figure 7:
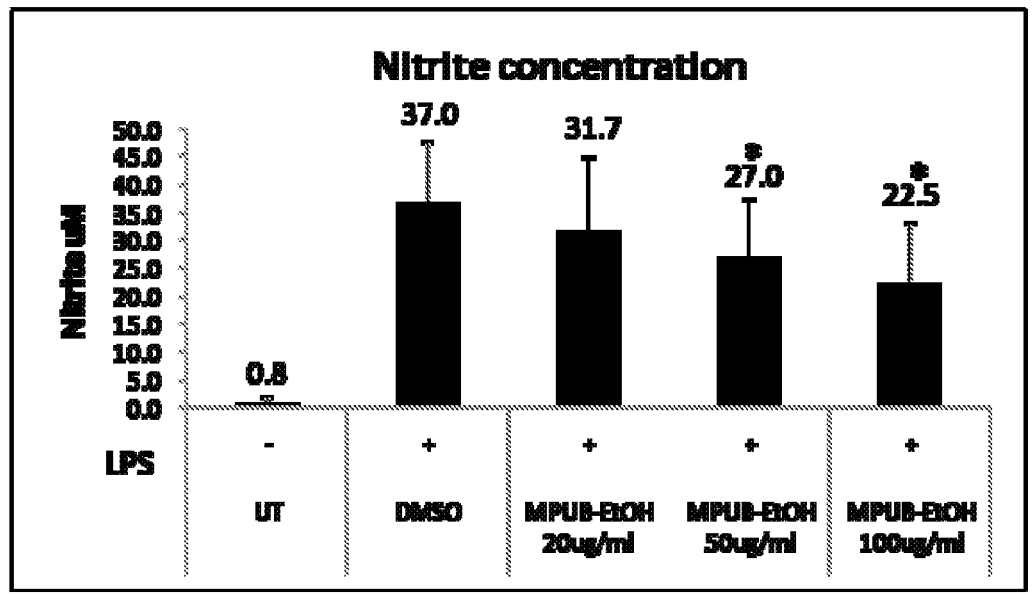
FIG. 7 shows that *C. versicolor* extract (MPUB-EtOH) reduced LPS-induced nitrite production. All data were plotted as mean values±SD of at least 3 independent experiments. A p value of <0.05 (*) was considered statistically significant.

To investigate the effect of *C. versicolor* extract (MPUB-EtOH) on LPS-induced nitrite production, mouse macrophages (RAW 264.7) were pretreated with MPUB-EtOH at various concentrations (20, 50 and 100 ug/ml) for 24 hrs. The cells were then treated with LPS (100 ng/ml) for 18 hrs, and nitrite concentrations (uM) were measured by Griess Reagent. As shown in FIG. 7, *C. versicolor* extract inhibited nitrite production in a dose-dependent manner.

Example 6—Determination of Antiviral Effects of *Coriolus Versicolor* Extract

To investigate the antiviral effects of *C. versicolor* extract, human neuronal cells (SKNSH) were pretreated with the MPUB-EtOH at 10 ug/ml for 18 hrs. Culture supernatants were reserved for sequential incubation. The cells were then infected with herpes simplex virus (HSV) at a m.o.i. (multiplicity of infection) of 0.01 for 1 hr. After viral infection, the cells were washed twice with PBS and incubated with the reserved culture supernatants for another 18 hrs. The culture supernatants were collected for determining viral titers, measured by the titration of tissue culture infectious dose$_{50}$ (TCID$_{50}$) during infection of T98G (human glioblastoma line) cells.

Figure 8A:
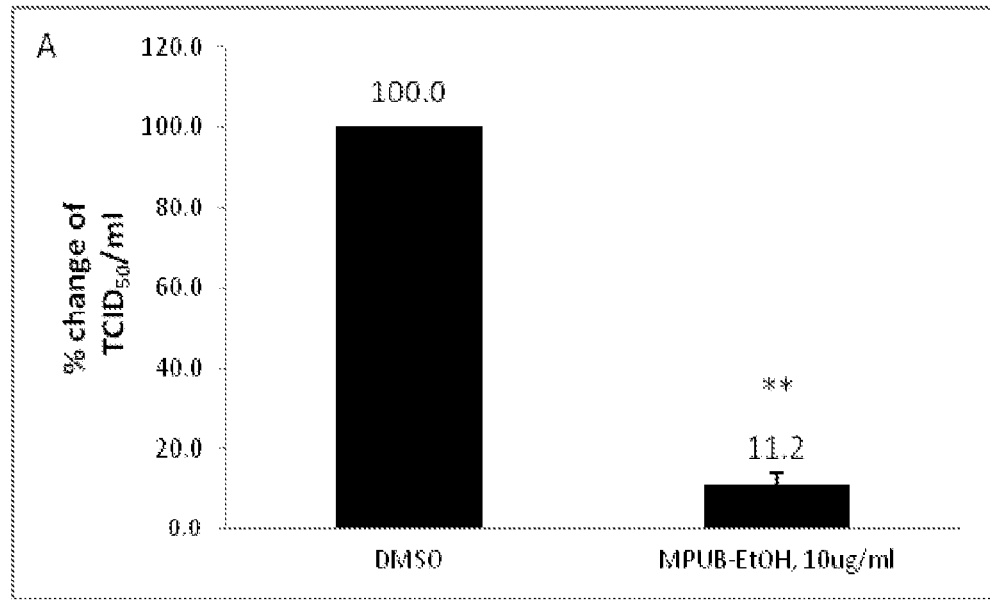
FIGS. 8A-C show the antiviral effects of *C. versicolor* extract (MPUB-EtOH). (A) shows the reduction of herpes simplex virus (HSV) viral titers by *C. versicolor* extract. The *C. versicolor* extract (MPUB-EtOH) was fractionated into fractions 1-5 as shown in FIG. 4. Fractions 4-5 were cytotoxic (data not shown), and thus, were not further examined for antiviral effects. (B) shows the reduction of HSV viral titers by fractions 1-3 of the *C. versicolor* extract (MPUB-EtOH). (C) shows the reduction of HSV viral titers by fraction 3 of the *C. versicolor* extract (MPUB-EtOH). A p value of <0.001 (**) was considered statistically significant.

MPUB-EtOH was further factionated into five fractions as described in Example 4. SKNSH cells were pretreated with MPUB-EtOH-1,-2 and -3, and infected with HSV virus as described above. The viral titers (TCID$_{50}$) of culture supernatants were measured. MPUB-EtOH-4 and -5 were cytotoxic to the cells (data not shown) and, thus, were not investigated further for antiviral effects. All data shown in FIGS. 8A and 8C were plotted as mean values±SD of at least 3 independent experiments. A p value of <0.001 (**) was considered statistically significant.

Figure 8B:
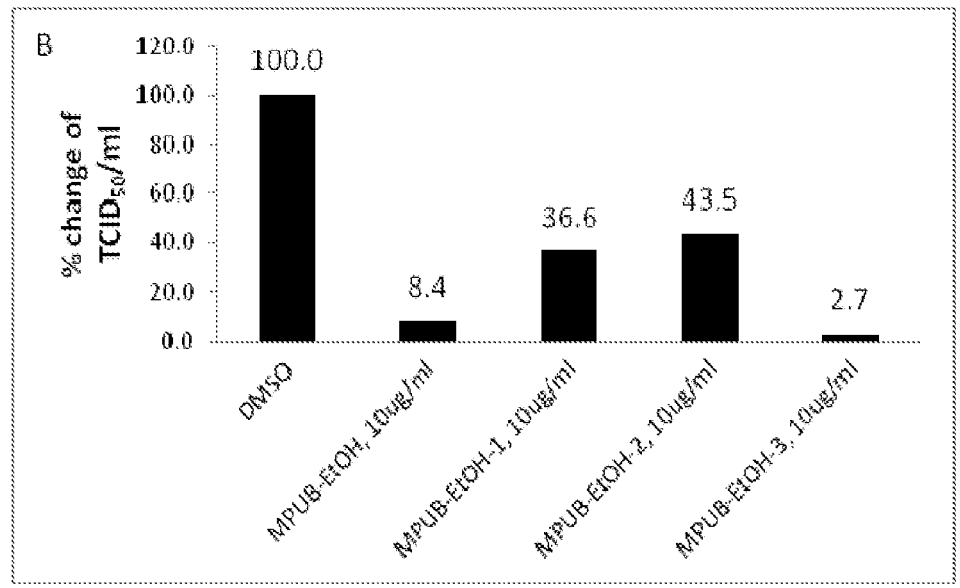
Figure 8C:
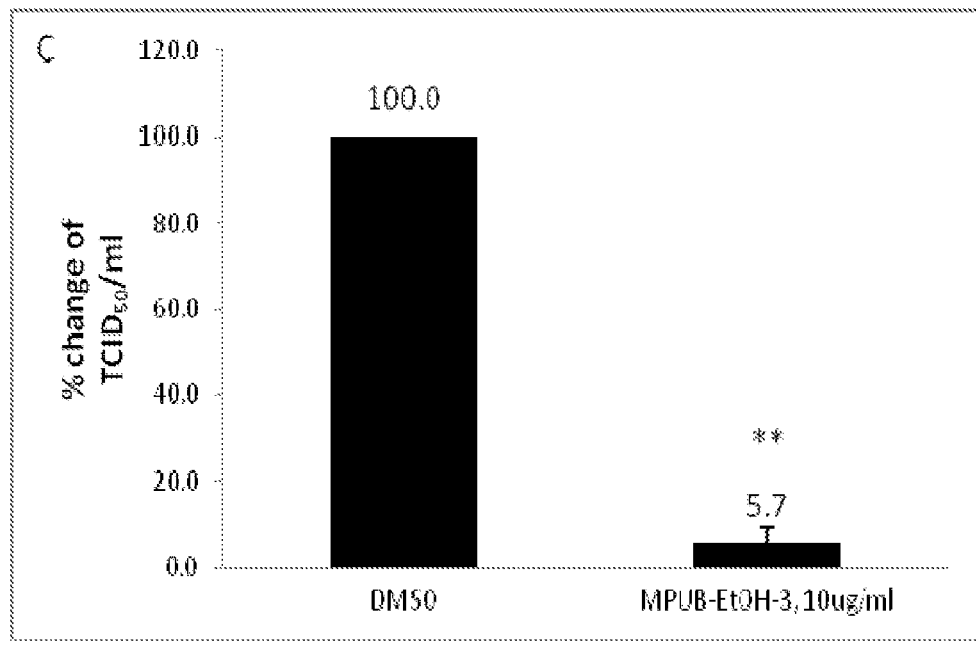

As shown in FIG. 8, the *C. versicolor* extract significantly reduced viral titers in culture supernatants, wherein fraction 3 exhibited the most potent antiviral effects (FIGS. 8B and 8C).

Example 7—Effects of *Coriolus Versicolor* Extract on MMP-3 Expression

Figure 9:
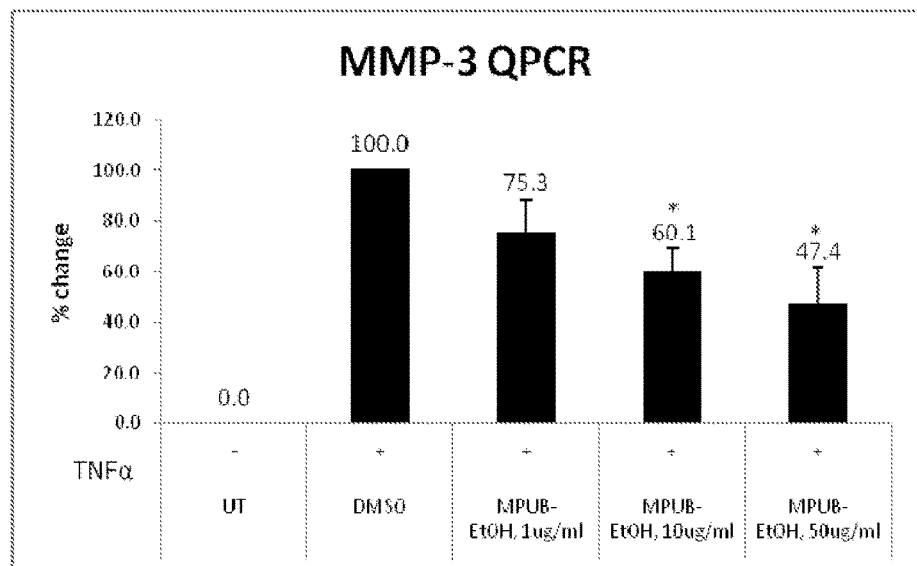
FIG. 9 shows that *C. versicolor* extract (MPUB-EtOH) reduced MMP-3 expression. A p value of <0.05 (*) was considered statistically significant.

This Example shows that *C. versicolor* extract reduces MMP-3 expression (FIG. 9). Briefly, glioblastoma (T98G, brain cells) cells were pretreated with MPUB-EtOH at different concentrations (1, 10 and 50 ug/ml) for 18 hrs, and then treated with recombinant human TNFα (10 ng/ml) for 3 hrs. MMP-3 mRNA levels were analyzed by TaqMan Gene Expression Assays. All data were plotted as mean values±SD of at least 3 independent experiments. A p value of <0.05 (*) was considered statistically significant.

Example 8—Determination of Antiviral Effects of *Coriolus Versicolor* Extract In Vivo To investigate the antiviral effects of *C. versicolor* extract in vivo, 3-week-old male BALB/c mice (15 mice per group) were administrated intraperitoneally (ip) with dimethyl sulfoxide (DMSO) (solvent for MPUB-EtOH) or MPUB-EtOH (250 mg/kg) once a day at 24 hr intervals for 7 days.

Briefly, the mice were infected with inoculation of HSV ip at 1×10$^5$ TCID$_{50}$/ml at day 0. DMSO, MPUB-EtOH or acyclovir (10 mg/kg) were administrated ip once a day at 24 hr intervals for 5 days starting 1 hr after infection. The mice were inspected daily and the disease severity was measured by hind-limb(s) paralysis based on the following scoring system: 0, no paralysis; 1, obvious difficulty in movement of hind limbs; 2, one hind limb incomplete paralysis; 3, one hind limb complete paralysis; 4, both hind limbs incomplete paralysis; 5, both hind limbs complete paralysis.

Figure 10:
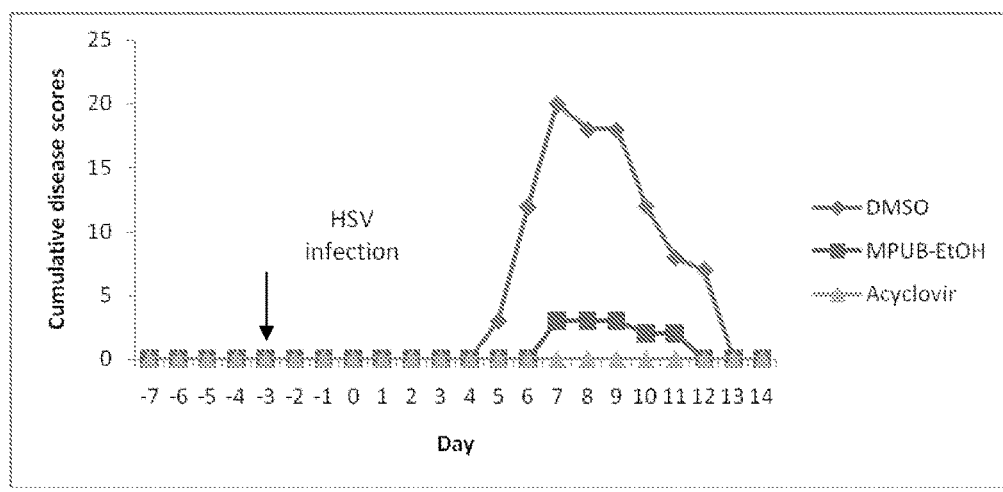
FIG. 10 shows that *C. versicolor* extract (MPUB-EtOH) reduced the severity of HSV infection in mice.

As shown in FIG. 10, *C. versicolor* extract (MPUB-EtOH) significantly reduced the severity of HSV infection in mice, as compared to the DMSO-treated controls. The antiviral effects of *C. versicolor* extract were comparable to that of acyclovir.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

1. Hobbs C (1995) Medicinal Mushrooms. Botanica Press, Botanica Press.
2. Ng T B (1998) A review of research on the protein-bound polysaccharide (Polysaccharopeptide, PSP) from the mushroom *Coriolus versicolor* (Basidiomycetes: Polyporaceae). *General Pharmacology* 30:1-4.
3. Guangdong Zyzbjwyh (1996) *Guangdong Zhong Yao Zhi*. Part 2. Guangzhou Shi: Guangdong kc ji chu ban she.
4. Yang Q Y, et al. (1992) Antitumor and Immunomodulating Activities of the Polysaccharide-Peptide (Psp) of *Coriolus*-Versicolor. *Eos-Rivista Di Immunologia Ed Immunofarmacologia* 12:29-34.
5. Sakagami H, Takeda M (1993) Diverse biological activity of PSK (Krestin), a protein-bound polysaccharide from *Coriolus versicolor* (Fr.) Quel, in: Chang S T, Buswell J A, Chiu S W (eds.). *Mushroom Biology and Mushroom Products*. Hong Kong: Chinese University Press:237-245.
6. Zhu P, Yang M P, Chen Z N (1993) Study on the inhibitory effect of purified PSP (PCV) on the respiratory syncytial virus, in: Yang Q Y, Kwok C Y (eds.). *Proceedings of PSP International Symposium*, Shanghai, China: Fudan University Press:153-154.
7. Collins R, Ng T B (1999) Polysaccharopeptide from *Coriolus versicolor* has potential for use against human immunodeficiency virus type 1 infection, in: Yang Q Y (ed.). *Advanced Research in PSP*, Hong Kong: Hong Kong Association for Health Care:181-186.
8. Sakagami H, Aoki T, Simpson A, Tanuma S (1991) Induction of immunopotentiation activity by a protein-bound polysaccharide, PSK (review). *Anticancer Res* 11:993-999.
9. Tsukagoshi S, et al. (1984) Krestin (Psk). *Cancer Treatment Reviews* 11:131-155.
10. Ueno S Y C, Omura Y, Fugii T, Wada T, Takahashi E, Hirose F (1987) U.S. Pat. No. 4,699,787: nitrogen-containing polysaccharide. October 13.
11. Ueno S Y C, Omura Y, Fugii T, Wada T, Takahashi E, Hirose F (1989) U.S. Pat. No. 4,851,395: nitrogen-containing polysaccharide. July 25.
12. Wang H X, Ng T B, Liu W K, Ooi V E C, Chang S T (1996) Polysaccharide-peptide complexes from the cultured mycelia of the mushroom *Coriolus versicolor* and their culture medium activate mouse lymphocytes and macrophages. *International Journal of Biochemistry & Cell Biology* 28:601-607.
13. Li X (1999) Advances in immunological studies in PSP, in: Yang Q Y (ed.). *Advanced Research in PSP*. Hong Kong: Hong Kong Association for Health Care:39-46.
14. Liu F, Ooi V E C, Fung M C (1999) Analysis of immunomodulating cytokines mRNAs in the mouse induced by mushroom polysaccharides. *Life Sci* 64:1005-1011.
15. Yang Q Y J S, Zhou X X Chen R T, Xu L Z (1992) Antitumor and immunomodulatoryactivities of the polysaccharide-peptide (PSP) of *Coriolus versicolor*. *Immunol Immunopharmac* 12:29-34.
16. Yang M P, Chen, G (1998) U.S. Pat. No. 5,824,648: Rnase-cv (*Coriolus versicolor*):October 20.
17. Gu Z, Liang Z Q, Wang X X (1999) Effect of *Coriolus versicolor* polysaccharopeptide on production of IL-6 from human peripheral blood lymphocytes, in: Yang Q Y (ed.). *Advanced Research in PSP*. Hong Kong: Hong Kong Association for Health Care:99-103.
18. Kobayashi H, Matsunaga K, Oguchi Y (1995) Antimetastatic Effects of Psk (Krestin), a Protein-Bound Polysaccharide Obtained from Basidiomycetes—an Overview. *Cancer Epidemiology Biomarkers & Prevention* 4:275-281.
19. Xu L (1999) The antitumor and anti-virus activity of polysaccharopeptide (PSP), in: Yang Q Y (ed.). *Advanced Research in PSP*. Hong Kong: Hong Kong Association for Health Care:62-67.
20. Yang Q, Hu Y J, Li X Y, Yang S X, Liu J X, Liu T F, Xu G M, Liao M L (1993) A new biological response modifier substance-PSP, in: Yang Q Y. Shanghai, China: Fudan University Press:247-259.
21. Yang M, Chen G (2000) U.S. Pat. No. 6,087,335: Rnase-cv (*Coriolus versicolor*):July 11.
22. Yang M, Chen Z N, Kwok J S L, Ge H (1992) The antitumor effect of a small polypeptide from *Coriolus versicolor* (SPCV). *Am J Chin Med* 20:221-232.
23. Dong Y, Yang M M P, Kwan C Y (1997) In vitro inhibition of proliferation of HL-60 cells by tetrandrine and *Coriolus versicolor* peptide derived from Chinese medicinal herds. *Life Sciences* 60:P1135-P1140.
24. Zhong B, Zhou Y G, Zhou L F, Qian Z B (1999) Genetic toxicity test of Yun Zhi polysaccharopeptide (PSP), in: Yang Q Y (ed.). *Advanced Research in PSP*, Hong Kong: Hong Kong Association for Health Care:285-294.
25. Lau C B S, et al. (2004) Cytotoxic activities of *Coriolus versicolor* (Yunzhi) extract on human leukemia and lymphoma cells by induction of apoptosis. *Life Sciences* 75:797-808.
26. Drozd J, Novák J P (1981) Chemical derivatization in gas chromatography. In: Journal of chromatography library, 2nd edn. Elsevier Scientific Publishing company. 19:165-174.
27. Yang C L, Chik S C, Li J C, Cheung B K, Lau A S (2009) Identification of the bioactive constituent and its mechanisms of action in mediating the anti-inflammatory effects of black cohosh and related *Cimicifuga* species on human primary blood macrophages. *J Med. Chem.* 52:6707-15.
28. Cheng S M, Li J C, Lin S S, Lee D C, Liu L, Chen Z, Lau A S (2009) HIV-1 transactivator protein induction of suppressor of cytokine signaling-2 contributes to dysregulation of IFN{gamma} signaling. *Blood.* 113:5192-201.
29. Law A H Y, Lee D C W, Cheung B K W, Yim H C H, Lau A S (2007) A Role for the nonstructural protein of SARS-CoV in Chemokine Dysregulation. *J Virology.* 81:416-22.
30. Lee D C, Yang C L, Chik S C, Li J C, Rong J H, Chan G C, Lau A S (2009) Bioactivity-guided identification and cell signaling technology to delineate the immunomodulatory effects of *Panax ginseng* on human promonocytic U937 cells. *J Transl Med.* 7:34.

We claim:

1. A method for treating a disease or condition selected from brain tumors; nasopharyngeal carcinomas; breast cancer; lung cancer; leukemia; lymphoma; colon cancer; stomach cancer; esophageal cancer; bladder cancer; gastric cancer; glioblastoma multiform; prostate cancer; and viral, bacterial, protozoan, fungal and microbial infections where the modulation of an immune response would be beneficial, wherein said method comprises administering, to a subject in need of such treatment, an effective amount of a composition comprising a *Coriolus versicolor* extract obtained by either:
   A) a method comprising the steps of:
      a) providing a sufficient quantity of raw material of *Coriolus versicolor*; and
      b) extracting biologically-active chemical constituents from the raw material of *Coriolus versicolor* with a polar solvent that is about 95% ethanol at a temperature of about 15° C. to about 30° C. to yield a *Coriolus versicolor* ethanol extract and a residue, and recovering the *Coriolus versicolor* ethanol extract;
   wherein step b) is performed once or more than once; or
   B) a method comprising the steps of:
      a) providing a sufficient quantity of raw material of *Coriolus versicolor*;
      b) extracting biologically-active chemical constituents from the raw material of *Coriolus versicolor* with a polar solvent that is about 95% ethanol to yield a *Coriolus versicolor* ethanol extract and a residue, and recovering the *Coriolus versicolor* ethanol extract, wherein step b) is performed once or more than once;
      c) extracting the residue obtained in step b) with an aqueous alkaline solution to yield an aqueous extract, and recovering said aqueous extract, wherein step c) is performed once or more than once; and d) combining one or more extracts obtained from steps b) and c) to yield *Coriolus versicolor* extract.

2. The method, according to claim 1, used to reduce IL-10 production and/or increase IFNβ production.

3. The method, according to claim 1, used to treat a brain tumor, nasopharyngeal carcinoma, breast cancer, lung cancer, leukemia, lymphoma, colon cancer, stomach cancer, esophageal cancer, bladder cancer, or gastric cancer.

4. The method, according to claim 1, used to treat glioblastoma multiforme, nasopharyngeal carcinoma, breast carcinoma, lung carcinoma, prostate cancer, or colon carcinoma.

5. The method, according to claim 1, used to treat infection by human immunodeficiency virus (HIV), influenza A virus, influenza B virus, human T-lymphotropic virus Type I (HTLV-1), bovine leukemia virus (BLV), Epstein-Barr virus, coronavirus, mycobacteria, *Staphylococcus aureus, Streptococcus pyogenes, Streptococcus pneumoniae, Escherichii coli, Listeria monocytogenes, L. amazonensis, Pneumocystis, Toxoplasma, Candida*, and/or *Aspergillus*.

6. The method, according to claim 1, used to treat infection by herpes simplex virus, varicella zoster, cytomegalovirus, and/or herpes virus-8.

* * * * *

UNITED STATES PATENT AND TRADEMARK OFFICE
CERTIFICATE OF CORRECTION

PATENT NO. : 10,226,493 B2
APPLICATION NO. : 13/876070
DATED : March 12, 2019
INVENTOR(S) : Allan Sik Yin Lau et al.

It is certified that error appears in the above-identified patent and that said Letters Patent is hereby corrected as shown below:

In the Specification

Column 1:
Lines 22-23, "Polyporaccae family." should read -- Polyporaceae family. --.

Column 3:
Line 6, "herpes virus-S." should read -- herpes virus-8 --.

Column 10:
Line 2, "absence f symptoms." should read -- absence of symptoms. --.

Column 12:
Line 4, "described in hooks" should read -- described in books --.

Column 16:
Line 33, "(Lichrospher 100 RP C18, EC Sum)," should read -- (Lichrospher 100 RP C18, EC 5um), --.

Signed and Sealed this
Twenty-seventh Day of August, 2019

Andrei Iancu
*Director of the United States Patent and Trademark Office*